(12) United States Patent
Neas et al.

(10) Patent No.: US 8,119,688 B2
(45) Date of Patent: Feb. 21, 2012

(54) DIFFERENTIAL EVAPORATION POTENTIATED DISINFECTANT SYSTEM

(75) Inventors: Edwin Dean Neas, Nunn, CO (US); Thomas Boyd Gilligan, Fort Collins, CO (US)

(73) Assignee: XY, LLC, Navasota, TX (US)

( * ) Notice: Subject to any disclaimer, the term of this patent is extended or adjusted under 35 U.S.C. 154(b) by 1019 days.

(21) Appl. No.: 11/901,915

(22) Filed: Sep. 19, 2007

(65) Prior Publication Data

US 2009/0076169 A1  Mar. 19, 2009

(51) Int. Cl.
*A61K 31/22* (2006.01)
*A61K 31/225* (2006.01)

(52) U.S. Cl. ........................................ 514/546; 514/547
(58) Field of Classification Search .................. 514/723, 514/546, 547
See application file for complete search history.

(56) References Cited

U.S. PATENT DOCUMENTS

| | | | |
|---|---|---|---|
| 1,654,103 A | 12/1927 | Thomson | |
| 3,226,211 A * | 12/1965 | Deffner et al. | 44/389 |
| 3,756,459 A | 9/1973 | Bannister et al. | |
| 4,201,764 A * | 5/1980 | French et al. | 424/45 |
| 4,796,788 A | 1/1989 | Bond | |
| 5,456,760 A | 10/1995 | Goehausen | |
| 5,492,534 A | 2/1996 | Athayde et al. | |
| 5,559,032 A | 9/1996 | Pomeroy et al. | |
| 5,665,315 A | 9/1997 | Robert et al. | |
| 5,672,764 A | 9/1997 | Teissier et al. | |
| 5,690,815 A | 11/1997 | Krasnoff et al. | |
| 5,799,830 A | 9/1998 | Carroll et al. | |
| 5,888,823 A | 3/1999 | Matsumoto et al. | |
| 5,893,843 A | 4/1999 | Rodrigues Claro | |
| 5,919,360 A | 7/1999 | Contaxis, III et al. | |
| 6,086,574 A | 7/2000 | Carroll et al. | |
| 6,248,343 B1 | 6/2001 | Jampani et al. | |
| 6,251,615 B1 | 6/2001 | Oberhardt | |
| 6,328,071 B1 | 12/2001 | Austin | |
| 6,495,366 B1 | 12/2002 | Briggs | |
| 6,593,283 B2 | 7/2003 | Hei et al. | |
| 6,698,627 B2 | 3/2004 | Garcia et al. | |
| 6,729,369 B2 | 5/2004 | Neas et al. | |
| 6,752,298 B2 | 6/2004 | Garcia et al. | |
| 6,761,286 B2 | 7/2004 | Py et al. | |
| 6,761,288 B2 | 7/2004 | Garcia | |
| 6,789,706 B2 | 9/2004 | Abergel et al. | |
| 6,789,750 B1 | 9/2004 | Heldt | |
| 6,793,387 B1 | 9/2004 | Neas et al. | |
| 6,855,678 B2 * | 2/2005 | Whiteley | 510/161 |
| 7,271,137 B2 * | 9/2007 | Tucker et al. | 510/110 |
| 2001/0023253 A1 | 9/2001 | Craig et al. | |
| 2001/0051379 A1 | 12/2001 | Pucher | |
| 2003/0095897 A1 | 5/2003 | Grate et al. | |
| 2003/0113673 A1 | 6/2003 | Ahn et al. | |
| 2003/0171242 A1 * | 9/2003 | Michaud et al. | 510/417 |
| 2004/0107150 A1 | 6/2004 | Neas et al. | |
| 2004/0246321 A1 | 12/2004 | Takashima et al. | |
| 2005/0003020 A1 | 1/2005 | Smith | |
| 2005/0011582 A1 | 1/2005 | Haug | |
| 2005/0031994 A1 | 2/2005 | Banba et al. | |
| 2005/0080194 A1 | 4/2005 | Satake et al. | |
| 2005/0209223 A1 | 9/2005 | Das et al. | |
| 2006/0118167 A1 | 6/2006 | Neas et al. | |
| 2006/0160712 A1 | 7/2006 | Hei et al. | |
| 2006/0229367 A1 | 10/2006 | Neas et al. | |
| 2006/0257436 A1 | 11/2006 | Kaminuma et al. | |
| 2006/0263399 A1 | 11/2006 | Yasuno et al. | |
| 2006/0293214 A1 | 12/2006 | Cheng et al. | |
| 2007/0053866 A1 | 3/2007 | Abou-Nemeh | |
| 2008/0090917 A1 | 4/2008 | Neas et al. | |

FOREIGN PATENT DOCUMENTS

WO  WO 2006/060770  6/2006
WO  WO 2006/110553  10/2006

OTHER PUBLICATIONS

U.S. Appl. No. 11/400,839, filed Apr. 6, 2006, entitled "Flow Path Conditioner System".
Conner et al., Vapor-Liquid Equilibria in Binary Systems, Industrial and Engineering Chemistry, vol. 42, No. 1, 1949, pp. 106-110.
Hack et al., Vapor-Liquid Equilibria of the Diacetone Alcohol-Water System at Subatmospheric Pressures, Industrial & Engineering Chemistry, vol. 46, No. 11, 1954, pp. 2392-2395.
Product Properties Test Guidelines, OPPTS 830.7200 Melting Point/ Melting Range, EPA, Prevention, Pesticides & Toxic Substances(7101), EPA712-C-96-033, Aug. 1996, 5 total pages.
Product Properties Test Guidelines, OPPTS 830.7200 Boiling Point/ Boiling Range, EPA, Prevention, Pesticides & Toxic Substances(TS7101), EPA712-C-96-034, Aug. 1996, 13total pages.
Document Summary, Active Standard:ASTM D7094-04 Standard Test Method for Flash Point by Modified Continuously Closed Cup (MCCCFP) Tester, http://www.astm.org, Aug. 16, 2007, 2 pp.
Slow-Stirring Method for Determining The n-Octanol/Water Partition Coefficient . . . , Environmental Toxicology & Chemistry, http://www.setacjournals.org, Aug. 16, 2007, pp. 1051-1057.
Germicidal Spray Products as Disinfectants, http://www.eoma.aoac.org/methods, Aug. 16, 2007, one page.
Sorting of Bacteria, Current Protocols in Cytometry, 1999, Supplement 7, Unit 11.4, pp. 11.4.1-11.4.12.
U.S. Appl. No. 60/669,912, filed Apr. 7, 2005.
Office Action mailed on May 6, 2008 for U.S. Appl. No. 11/400,839; 13 pages. Office Action mailed on Aug. 19, 2008 for U.S. Appl. No. 11/400,839; 12 pages.
Office Action mailed on May 13, 2009 for U.S. Appl. No. 11/400,839; 24 pages.
Office Action mailed on Feb. 3, 2010 for U.S. Appl. No. 11/400,839; 20 pages.

* cited by examiner

*Primary Examiner* — Shengjun Wang
(74) *Attorney, Agent, or Firm* — Craig R. Miles; CR Miles, P.C.

(57) ABSTRACT

Antimicrobial compositions and methods of using such antimicrobial compositions to provide a reduction in populations of viable microorganisms.

10 Claims, 24 Drawing Sheets

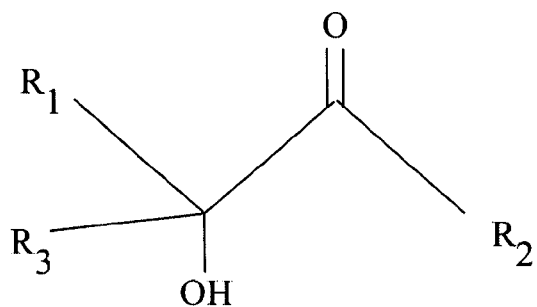

3-hydroxy-2-butanone ($R_1$ = $CH_3$, $R_2$ = $CH_3$, $R_3$ = H)
3-hydroxy-2-pentanone ($R_1$ = $CH_2CH_3$, $R_2$ = $CH_3$, $R_3$ = H)
2-hydroxy-3-pentanone ($R_1$ = $CH_3$, $R_2$ = $CH_2CH_3$, $R_3$ = H)
3-hydroxy-3-methyl-2-pentanone ($R_1$ = $CH_2CH_3$, $R_2$ = $CH_3$, $R_3$ = $CH_3$)
3-hydroxy-4-methyl-2-pentanone ($R_1$ = $CH_2(CH_3)_2$, $R_2$ = $CH_3$, $R_3$ = H)
4-hydroxy-2-methyl-3-pentanone ($R_1$ = $CH_3$, $R_2$ = $CH_2(CH_3)_2$, $R_3$ = H)
3-hydroxy-2-hexanone ($R_1$ = $CH_2CH_2CH_3$, $R_2$ = $CH_3$, $R_3$ = H)
4-hydroxy-3-hexanone ($R_1$ = $CH_2CH_3$, $R_2$ = $CH_2CH_3$, $R_3$ = H)
4-hydroxy-4-methyl-3-hexanone ($R_1$ = $CH_2CH_3$, $R_2$ = $CH_2CH_3$, $R_3$ = $CH_3$)
4-hydroxy-5-methyl-3-hexanone ($R_1$ = $(CH_3)_2$, $R_2$ = $CH_2CH_3$, $R_3$ = H)
4-hydroxy-3-heptanone ($R_1$ = $CH_2CH_2CH_3$, $R_2$ = $CH_2CH_3$, $R_3$ = H)
4-hydroxy-5-octanone. ($R_1$ = $CH_2CH_2CH_3$, $R_2$ = $CH_2CH_2CH_3$, $R_3$ = H)

FIG.4

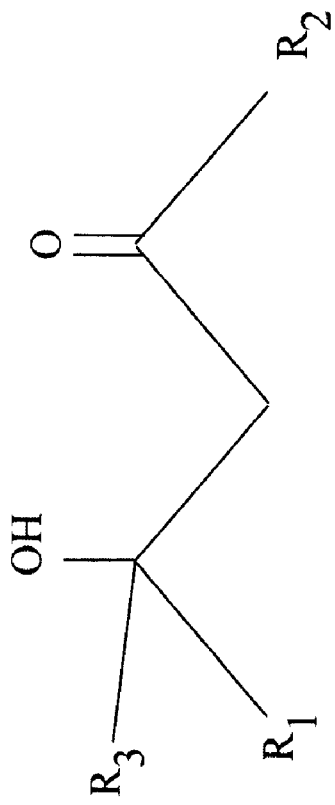

4-hydroxy-2-butanone ($R_1$ = H, $R_2$ = $CH_3$, $R_3$ = H)
4-hydroxy-2-pentanone ($R_1$ = $CH_3$, $R_2$ = $CH_3$, $R_3$ = H)
1-hydroxy-3-pentanone ($R_1$ = H, $R_2$ = $CH_2CH_3$, $R_3$ = H)
4-hydroxy-4-methyl-2-pentanone (DAA) ($R_1$ = $CH_3$, $R_2$ = $CH_3$, $R_3$ = $CH_3$)
4-hydroxy-2-hexanone ($R_1$ = $CH_2CH_3$, $R_2$ = $CH_3$, $R_3$ = H)
5-hydroxy-4-methyl-3-hexanone ($CH_3CH_2OHCH_2CH(CH_3)COCH_2CH_3$)
5-hydroxy-5-methyl-3-hexanone ($R_1$ = $CH_3$, $R_2$ = $CH(CH_3)$, $R_3$ = $CH_3$)
5-hydroxy-3-heptanone ($R_1$ = H, $R_2$ = $CH_2CH_3$, $R_3$ = $CH_3CH_2$)
5-hydroxy-5-methyl-3-heptanone ($R_1$ = $CH_3$, $R_2$ = $CH_2CH_3$, $R_3$ = $CH_3CH_2$)
3-hydroxy-3-methyl-5-heptanone ($R_1$ = $CH_3$, $R_2$ = $CH_2CH_2$, $R_3$ = $CH_3CH_2$)
4-hydroxy-3,4-dimethyl-2-hexanone ($R_1$ = $CH_3$, $R_2$ = $CH_2CH_2CH_2CH_3$, $R_3$ = $CH_3CH_2CH_2$ $CH_2$)

FIG.5 ethylene glycol monoethyl ether ($R_1 = CH_2CH_3$)
ethylene glycol monopropyl ether ($R_1 = CH_2CH_2CH_3$)
ethylene glycol monobutyl ether (EGMBE) ($R_1 = CH_2CH_2CH_2CH_3$)
ethylene glycol monopentyl ether ($R_1 = CH_2CH_2CH_2CH_2CH_3$)
ethylene glycol monohexyl ether. ($R_1 = CH_2CH_2CH_2CH_2CH_2CH_3$)

ethylene glycol dimethyl ether ($R_1 = CH_3$, $R_2 = CH_3$)
ethylene glycol diethyl ether ($R_1 = CH_2CH_3$, $R_2 = CH_2CH_3$)
ethylene glycol dipropyl ether ($R_1 = CH_2CH_2CH_3$, $R_2 = CH_2CH_2CH_3$)

ethylene glycol monomethyl ether acetate (EGMEA) ($R_1$ = $CH_3$, $R_2$ = $CH_3$)
ethylene glycol monoethyl ether acetate ($R_1$ = $CH_3$, $R_2$ = $CH_2CH_3$)
ethylene glycol monomethyl ether butyrate ($R_1$ = $CH_2CH_2CH_3$, $R_2$ = $CH_3$)
ethylene glycol monoethyl ether butyrate ($R_1$ = $CH_2CH_2CH_3$, $R_2$ = $CH_2CH_3$)

propylene glycol monomethyl ether ($R_1$ = $CH_3$)
propylene glycol monoethyl ether ($R_1$ = $CH_2CH_3$)
propylene glycol monopropyl ether ($R_1$ = $CH_2CH_2CH_3$)
propylene glycol monobutyl ether ($R_1$ = $CH_2CH_2CH_2CH_3$)
propylene glycol monopentyl ether ($R_1$ = $CH_2CH_2CH_2CH_2CH_3$)

propylene glycol dimethyl ether ($R_1$ = $CH_3$, $R_2$ = $CH_3$)
propylene glycol diethyl ether ($R_1$ = $CH_2CH_3$, $R_2$ = $CH_2CH_3$)

propylene glycol monomethyl ether acetate ($R_1 = CH_3$, $R_2 = CH_3$)
propylene glycol monoethyl ether acetate ($R_1 = CH_3$, $R_2 = CH_2CH_3$)
propylene glycol monomethyl ether butyrate ($R_1 = CH_2CH_2CH_3$, $R_2 = CH_3$)

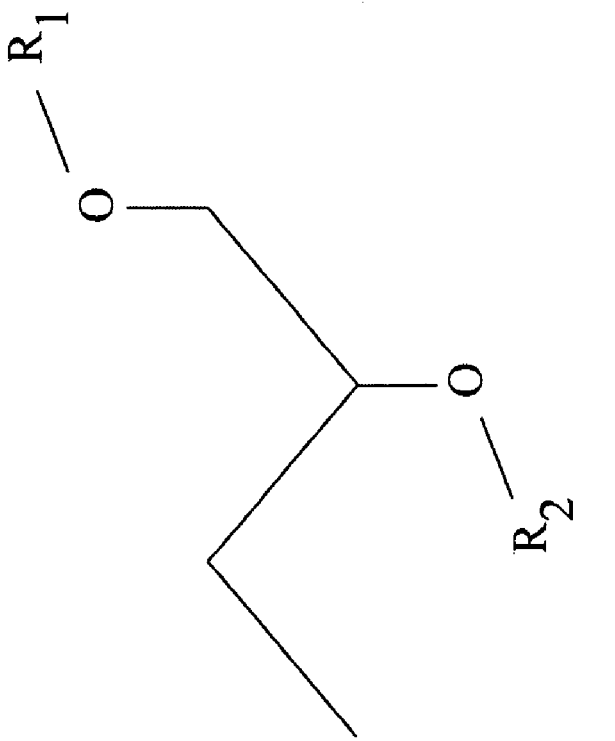
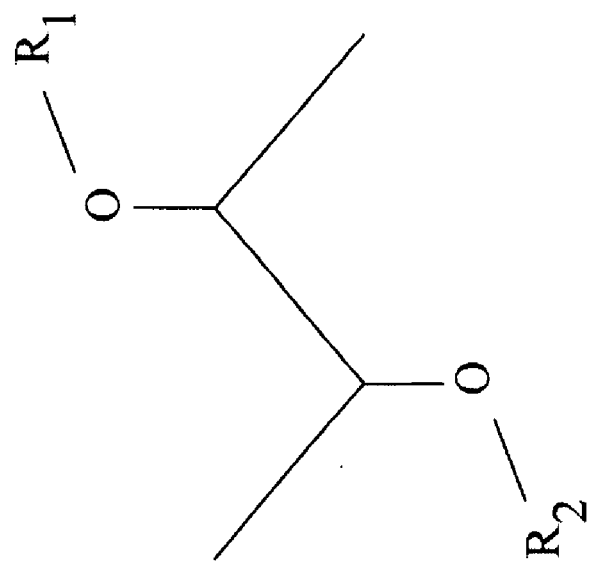
butylene glycol dimethyl ether ($R_1 = CH_3$, $R_2 = CH_3$)
butylene glycol diethyl ether ($R_1 = CH_2CH_3$, $R_2 = CH_3CH_2$)
FIG.13 butylene glycol monomethyl ether formate ester ($R_1 = CH_3$, $R_2 = (CO)H$)
butylene glycol monoethyl ether acetate. ($R_1 = CH_2CH_3$, $R_2 = (CO)CH_3$) or
($R_2 = CH_2CH_3$, $R_1 = (CO)CH_3$)

ethylene glycol monoethyl ester ($R_1 = CH_3$)
ethylene glycol monopropyl ester ($R_1 = CH_2CH_3$)
ethylene glycol monobutyl ester ($R_1 = CH_2CH_2CH_3$)
ethylene glycol monopentyl ester ($R_1 = CH_2CH_2CH_2CH_3$)
ethylene glycol monohexyl ester. ($R_1 = CH_2CH_2CH_2CH_2CH_3$)

ethylene glycol dimethyl ester ($R_1$ = H, $R_2$ = H)
ethylene glycol diethyl ester (EGDA) ($R_1$ = $CH_3$, $R_2$ = $CH_3$)
ethylene glycol dipropyl ester ($R_1$ = $CH_2CH_3$, $R_2$ = $CH_3CH_2$)

propylene glycol monomethyl ester ($R_1$ = H)
propylene glycol monoethyl ester ($R_1$ = $CH_3$)
propylene glycol monopropyl ester ($R_1$ = $CH_2CH_3$)
propylene glycol monobutyl ester ($R_1$ = $CH_2CH_2CH_3$)
propylene glycol monopentyl ester ($R_1$ = $CH_2CH_2CH_2CH_3$)

propylene glycol dimethyl ester ($R_1$ = H, $R_2$ = H)
propylene glycol diethyl ester ($R_1$ = $CH_3$, $R_2$ = $CH_3$)
propylene glycol dipropyl ester ($R_1$ = $CH_2CH_3$, $R_2$ = $CH_3CH_2$)
propylene glycol dibutyl ester ($R_1$ = $CH_2CH_2CH_3$, $R_2$ = $CH_3CH_2 CH_2$)
propylene glycol dipentyl ester ($R_1$ = $CH_2CH_2CH_2CH_3$, $R_2$ = $CH_3CH_2 CH_2CH_2$)

butylene glycol dimethyl ester ($R_1$ = H, $R_2$ = H)
butylene glycol diethyl ester ($R_1$ = $CH_3$, $R_2$ = $CH_3$)
butylene glycol dipropyl ester ($R_1$ = $CH_2CH_3$, $R_2$ = $CH_3CH_2$)
butylene glycol dibutyl ester ($R_1$ = $CH_2CH_2CH_3$, $R_2$ = $CH_3CH_2 CH_2$)

butylene glycol methyl ester ($R_1$ = H)
butylene glycol ethyl ester ($R_1$ = $CH_2CH_3$, $R_2$ = H )

acetone oxime ($R_1 = CH_3$, $R_2 = CH_3$)
methylethylketone oxime (MEKO) ($R_1 = CH_2CH_3$, $R_2 = CH_3$)
2-pentanone oxime ($R_1 = CH_2CH_2CH_3$, $R_2 = CH_3$)
3-pentanone oxime ($R_1 = CH_2CH_3$, $R_2 = CH_3CH_2$)
cyclopentanone oxime ($R_1 = R_2 = CHCH_2CH_2CH$)
2-hexanone oxime ($R_1 = CH_3$, $R_2 = CH_3CH_2CH_2CH_2$)
3-hexanone oxime ($R_1 = CH_2CH_2$, $R_2 = CH_3CH_2\ CH_2$)
cyclohexanone oxime ($R_1 = R_2 = CHCH_2CH_2CH_2CH$)

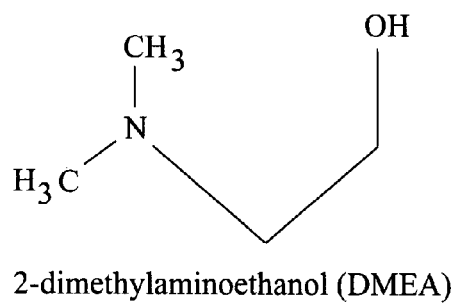
2-dimethylaminoethanol (DMEA)
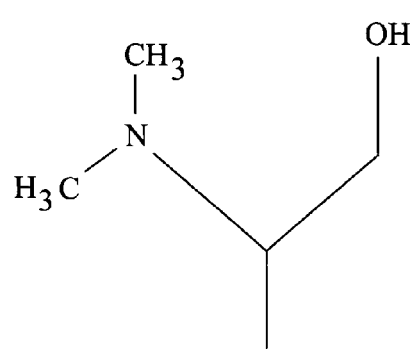
2-dimethylamino-1-propanol
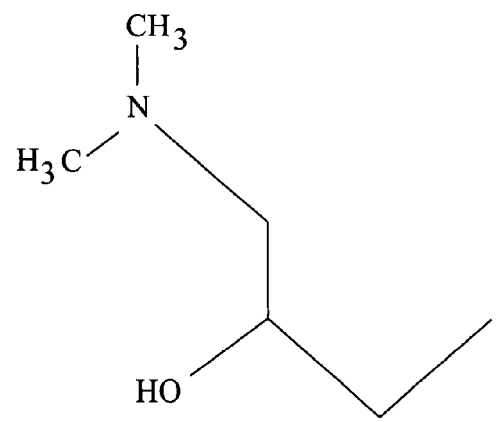
1-dimethylamino-2-butanol
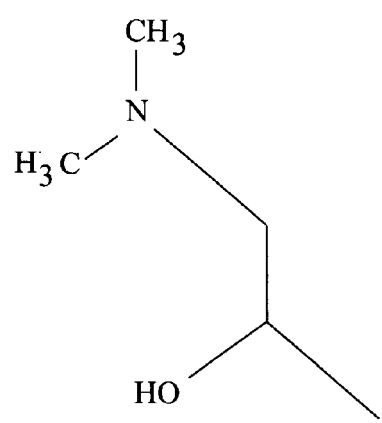
1-dimethylamino-2-propanol
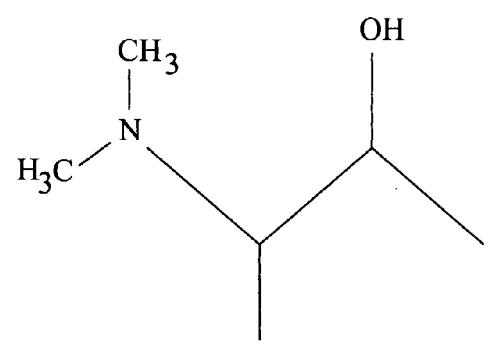
3-dimethylamino-2-butanol
FIG.22 pyridine ($R_1$ = H, $R_2$ = H, $R_3$ = H)
2-methylpyradine ($R_1$ = $CH_3$, $R_2$ = H, $R_3$ = H)
3-methylpyradine ($R_1$ = H, $R_2$ = $CH_3$, $R_3$ = H)
4-methylpyradine ($R_1$ = H, $R_2$ = H, $R_3$ = $CH_3$)

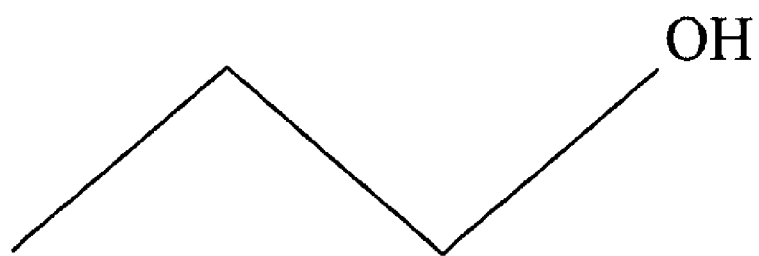
1 - butanol
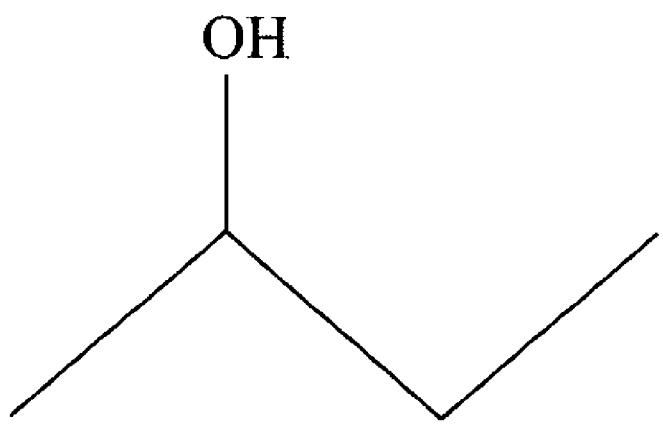
2 - butanol
FIG.24

DIFFERENTIAL EVAPORATION POTENTIATED DISINFECTANT SYSTEM

I. TECHNICAL FIELD

Differential evaporation potentiated antimicrobial compositions and methods of using such differential evaporation potentiated antimicrobial compositions to provide a reduction in populations of viable microorganisms.

II. BACKGROUND

Alcohols have been extensively utilized in antimicrobial formulations to provide a reduction in populations of viable microorganisms. Methanol, ethanol, and N-butanol can each be produced by fermentation and alcohols such as 2-propanol, 2-butanol, 2-pentanol, and so on, can be synthesized from petrochemicals.

Because 2-propanol (also referred to as isopropanol) has proven more effective than ethanol and methanol in reducing populations of viable microorganisms its use has become widespread in conventional antimicrobial formulations. The superior efficacy of isopropanol over methanol and ethanol can be understood, in part, by considering the physical properties as summarized in TABLE 1.

TABLE 1

| Chemical | Log P | Azeotrope with Water | | FP |
| --- | --- | --- | --- | --- |
| | | % w/w | % v/v | |
| Methanol | −0.70 | NA | NA | 11° C. |
| Ethanol | −0.30 | 95% | 94% | 22° C. |
| Acetone | −0.23 | NA | NA | −18° C. |
| Isopropanol | 0.05 | 87% | 83% | 21° C. |

The effect of the alcohol as an antimicrobial material may in part be related to concentration and in part duration of time in contact with the target microbe. Additionally, the effectiveness of an alcohol or other antimicrobial material in reducing populations of microorganisms may also be due to its log P, also referred to as the Log $P_{ow}$. Log $P_{ow}$ is the $\log_{10}$ of the ratio of the equilibrium concentrations of the alcohol or other antimicrobial material in 1-octanol saturated with water (COi) and water saturated with 1-octanol (CWi). Log $P_{ow}=\log_{10}(COi/CWi)$. Negative values of Log $P_{ow}$ represent substances that are more soluble in water, while positive values of Log $P_{ow}$ represent substances that are more soluble in n-octanol. In general, the more soluble an antimicrobial material is in n-octanol the more effective the antimicrobial material may be in reducing populations of microorganisms in aqueous solutions. It may be predicted that isopropanol will be a more effective antimicrobial than methanol, ethanol, and acetone based on the Log $P_{ow}$.

While alcohols such as methanol, ethanol, and isopropanol and ketones such as acetone have proven effective in reducing viable populations of microorganisms, certain substantial problems remain unaddressed with their use.

A first substantial problem with the use of certain alcohols such as methanol and certain ketones such as acetone in or as compositions for the reduction of viable populations of microorganisms can be their relatively high vapor pressures and relatively low flashpoints (FP). In this regard, alcohols and ketones conventionally included in antimicrobial compositions can have vapor pressures and flashpoints which allow ignition even without direct contact with the ignition source and may be regulated as workplace hazards. Additionally, alcohols and ketones conventionally used as or in antimicrobial compositions may have to be shipped as flammable materials under United States Department of Transportation ("DOT") guidelines. Flammable materials can be more costly to transport than materials which are not characterized as flammable under DOT guidelines.

Another substantial problem with the use of alcohols such as methanol, ethanol and isopropanol and ketones such as acetone can be that upon application to viable populations of microorganisms the rate of evaporation can limit the duration of time a viable population of microorganisms is exposed to alcohol or ketone. Even as aqueous mixtures, alcohols and ketones can evaporate from the aqueous mixture at a rate which alters the efficacy of the mixture as the concentration of the alcohol or ketone in the mixture reduces over time.

The instant invention provides a differential evaporation potentiated disinfectant system which provides antimicrobial compositions and methods of using such antimicrobial compositions to potentiate the active components of the composition for the reduction of viable populations of microorganisms in conditioning, cleaning or disinfection of surfaces.

III. SUMMARY OF THE INVENTION

Accordingly, a broad object of the invention can be to provide a differential evaporation potentiated disinfectant system which includes differential evaporation potentiated antimicrobial compositions and methods of using such differential evaporation potentiated antimicrobial compositions to reduce populations of viable microorganisms.

The terms "disinfectant" means a composition which upon engagement with a population of viable microorganisms provides greater than a 2-$\log_{10}$ order reduction (greater than 99% reduction) in the population of viable microorganisms (also referred to herein as an "antimicrobial composition"). The term "disinfection" means a greater than a 2-$\log_{10}$ order reduction (greater than 99% reduction) in the population of viable microorganisms. The term "viable microorganism" means a microorganism capable of reproduction. The term "reduction in the population of viable microorganisms" means rendering all or a portion of a population of microorganisms incapable of reproduction whether achieved by killing all or a portion of the population of microorganisms or otherwise incapacitating reproduction of all or a portion of the population of microorganisms. The term "differential evaporation potentiated" means a maintenance or increase in the concentration of the antimicrobially active agent(s) included in a composition due to the greater rate of evaporation of the inactive agent(s) included in the composition providing a greater than 2-$\log_{10}$ order reduction in the population of viable microorganisms, whether upon application or after elapse of a duration of time after application to a viable population of microorganisms.

A second broad object of the invention can be to provide differential evaporation potentiated antimicrobial compositions which include a mixture of an amount of antimicrobially active agent and an amount of inactive agent each soluble in the other and each establishing an equilibrium between the liquid and vapor phase in accordance with Raoult's law which results in maintenance or an increase in concentration of the antimicrobially active agent over a duration of time. While certain embodiments of the differential evaporation potentiated antimicrobial compositions may include an amount of one antimicrobially active agent and an amount of one inactive agent the invention is not so limited and the amount of antimicrobial agent can include at least one antimicrobially active agent or a plurality of antimicrobially active agents and the amount of inactive agent can include at least one inactive agent or a plurality of inactive agents the concentrations established in various permutations and combinations which afford a differential evaporation potentiated antimicrobial composition. As shown by FIG. 1, the relationship of the concentrations in liquid phase and vapor phase for one constituent in a mixture which comes to equilibrium in accordance with Raoult's law is represented by line A.

A third broad object of the invention can be to provide differential evaporation potentiated antimicrobial compositions which include a mixture of an amount of antimicrobially active agent and an amount of inactive agent each soluble in the other and each establishing an equilibrium between the liquid and vapor phase as an azeotrope which results in maintenance or an increase in concentration of the antimicrobially active agent over a duration of time. Again, while certain embodiments of the differential evaporation potentiated antimicrobial compositions may include an amount of one antimicrobially active agent and an amount of one inactive agent the invention is not so limited and the amount of antimicrobial agent can include at least one antimicrobially active agent or a plurality of antimicrobially active agents and the amount of inactive agent can include at least one inactive agent or a plurality of inactive agents the concentrations established in various permutations and combinations which as an azeotrope affords a differential evaporation potentiated antimicrobial composition. As shown by FIG. 1, the relationship of the concentrations in liquid phase and vapor phase for one constituent in a mixture which comes to equilibrium from an azeotropic composition is shown by lines B and G.

As a non-limiting example, Line G represents the equilibrium between the liquid phase and the vapor phase of a binary azeotrope composition including an amount of diacetone alcohol combined with an amount of water as a non-limiting example. Point H on Line, G represents the azeotrope point, which for the particular example of diacetone alcohol may correspond to a concentration of about 12.7 grams of diacetone alcohol per 100 grams of the combination of diacetone alcohol and water, or about 13.4% diacetone alcohol volume to volume ("v/v"). A composition established at the azeotrope when evaporated produces a vapor having the same ratio of constituents as the original concentration of the composition as a liquid. However, an initial concentration of diacetone alcohol such as 20% (v/v) (Point J on Line G) in water will cause a shift in the vapor-equilibrium to the right on Line G towards point K and point L, where the differential loss of water to the vapor phase increases. Conversely, an initial concentration of diacetone alcohol such as 10% (v/v) will cause a shift in the vapor-equilibrium to the left on Line G, where the differential loss of diacetone alcohol to the vapor phase increases.

Based on the azeotropre point of 13.4% (v/v) (H) shown in FIG. 1, for example, an initial concentration of diacetone alcohol such as 10% (v/v) in water does not define an antimicrobial composition then evaporation of all or a part of the amount of the diacetone alcohol and water composition fluidically engaged with a population of microorganisms will not increase the concentration of the diacetone alcohol in the composition, but rather over a duration of time the concentration of diacetone alcohol in water will decrease. Accordingly, an initial concentration of 10% (v/v) diacetone alcohol in water may not be potentiated, at standard atmospheric pressure, toward an antimicrobially active composition to reduce the population of viable microorganisms.

Conversely, if an initial concentration of diacetone alcohol which exceeds the azeotrope point in water does not define an antimicrobial composition but a greater concentration of diacetone alcohol does define an antimicrobial composition, then evaporation of all or a part of the amount of the diacetone alcohol and water composition fluidically engaged with a population of microorganisms can increase the concentration of the diacetone alcohol in the composition over a duration of time and the composition can be potentiated to provide an antimicrobially active composition which can reduce the population of viable microorganisms.

Additionally, if an initial concentration of diacetone alcohol which exceeds the azeotrope point in water defines an antimicrobial composition, then evaporation of all or a part of the amount of the diacetone and water composition can increase the concentration of the diacetone alcohol in the antimicrobial composition over a duration of time. Accordingly, evaporation of an amount of the antimicrobial composition can occur without loss of antimicrobial activity and the antimicrobial composition can be potentiated to provide an increased level of antimicrobial activity as compared with the initial concentration of the antimicrobial composition.

A fourth broad object of the invention can be to provide differential evaporation potentiated antimicrobial compositions which are as effective or more effective in reducing populations of microorganisms as compared to conventional antimicrobial compositions. Now referring primarily to Table 2 and FIG. 1, it can be understood that a conventional antimicrobial composition of 70% isopropanol in water is well below the azeotrope point of about 87.40% (w/w) or 89.83% (v/v) (see Line B, point C). Accordingly, evaporation of all or a part of the amount of a conventional isopropanol in water antimicrobial composition can shift the liquid-vapor equilibrium to the left toward points D, E, and F on Line B and the concentration of isopropanol in the liquid phase can decrease over a duration of time. As a result, the level of antimicrobial efficacy of such amounts of isopropanol in water upon evaporation can be reduced or lost over the duration of time. Conversely, the inventive differential evaporation potentiated antimicrobial composition of 15% (v/v or w/w) diacetone alcohol is well above the azeotrope point of about 12.70 (w/w) or 13.43% (v/v). Additionally, it takes a lesser percent of the antimicrobially active agent per volume of composition to prepare this particular embodiment of an inventive differential evaporation potentiated antimicrobial composition of 15% (v/v) diacetone alcohol in water than to prepare the conventional antimicrobial composition of 70% (v/v) isopropanol in water.

TABLE 2

| | Molecular Weight (g/mole) | Density (g/ml) | azeotrope % mol/mol | azeotrope % w/w | azeotrope % vol/vol |
|---|---|---|---|---|---|
| AZEOTROPE OF ISOPROPANOL IN WATER | | | | | |
| Isopropanol | 60 | 0.785 | 67.5% | 87.40% | 89.83% |
| $H_2O$ | 18 | 1.000 | 32.5% | 12.60% | 10.17% |
| AZEOTROPE OF DIACETONE ALCOHOL IN WATER | | | | | |
| Diacetone Alcohol | 116 | 0.938 | 2.2% | 12.70% | 13.43% |
| $H_2O$ | 18 | 1.000 | 97.8% | 87.30% | 86.57% |

Now referring primarily to FIG. 2, Line A shows the change in fluid volume of 70% (v/v) isopropanol in water (a conventional antimicrobial composition) caused by evaporation, while line B represents the change in fluid phase concentration of the same 70% (v/v) isopropanol in water occurring during the same fluid volume change. As to this particular example, complete evaporation of an amount of 70% (v/v)

isopropanol in water can occur over about 15 time units. Line C represents the change in fluid volume of a 20% (v/v) solution of diacetone alcohol in water caused by evaporation (a particular embodiment of the inventive differential evaporation antimicrobial composition), while line D represents the change in fluid phase concentration of the same 20% (v/v) diacetone alcohol in water occurring during the same fluid volume change. In this case, complete evaporation can occur in approximately 75 time units. Comparatively, the 20% (v/v) diacetone alcohol in water can be engaged with a population of microorganisms for a greater duration of time than the conventional antimicrobial composition without reapplication of an additional amount because evaporation occurs at a slower rate as shown by Table 3.

TABLE 3

Relative Evaporation Rates

| ethanol | 2.80 | 70% (v/v) isopropanol (estimated) | 1.68 |
| isopropanol | 2.10 | 40% (v/v) diacetone alcohol (estimated) | 0.27 |
| acetone | 11.60 | 20% (v/v) diacetone alcohol (estimated) | 0.31 |
| diacetone alcohol | 0.14 | 10% (v/v) 2-butoxyethanol (estimated) | 0.33 |
| 2-butoxyethanol | 0.06 | 20% (v/v) 2-butoxyethanol (estimated) | 0.30 |
| water | 0.36 | | |
| BuAc (reference) | 1.00 | | |

Again referring primarily to FIG. 2, Line B, if 10% (v/v) isopropanol provides the minimum effective concentration to provide any reduction in a population of viable microorganisms, then the concentration of isopropanol remaining during the last 2-5 time units may not afford any additional reduction in the population of viable microorganisms because the concentration of isopropanol in the composition has been reduced by evaporation to less than 10% (v/v). By comparison, Line C represents the change in fluid volume of a 20% (v/v) solution of diacetone alcohol in water, while line D represents the change in concentration of diacetone alcohol in water. As to this non-limiting example, if 10% diacetone alcohol (v/v) is the minimum concentration to provide an antimicrobial composition, then the entire 75 time units provide an antimicrobial composition because the concentration of diacetone alcohol increases over the 75 time units in accordance with embodiments of differential evaporation potentiated antimicrobial compositions.

A fifth broad object of the invention can be to provide differential evaporation potentiated antimicrobial compositions which use one or a plurality of antimicrobially active agent(s) that have a Log P between about −1.0 and +1.0 or in a preferred range of about −0.30 and about +1.0. Solvents with Log P values above about 1.0 or 1.5 are usually not miscible with water and can be tolerated by certain kinds of microorganism. Substances such as sugars, amino acids, and other highly-water soluble materials, that have large negative Log P values, are also typically tolerated by most microorganisms. One non-limiting example of an embodiment of the inventive differential evaporation potentiated antimicrobial composition provides 20% (v/v) diacetone alcohol (CAS 123-42-2) which has a Log P of about −0.14. By comparison, while the Log P of isopropanol of about +0.05 compares favorably with 20% (v/v) diacetone alcohol in water, mixtures of isopropanol in water have all of the disadvantages above-discussed.

A sixth broad object of the invention can be to provide a method by which differential evaporation potentiated antimicrobial compositions can be identified from a numerous and varied group of substances.

Naturally, further objects of the invention are disclosed throughout other areas of the specification, drawings, and claims.

III. A BRIEF DESCRIPTION OF THE DRAWINGS

FIG. 4 provides chemical structures for particular alpha hydroxyketones which can be utilized to produce embodiments of the inventive differential evaporation potentiated disinfection system.

FIG. 5 provides chemical structures for particular beta hydroxyketones which can be utilized to produce embodiments of the inventive differential evaporation potentiated disinfection system.

Figure 6:
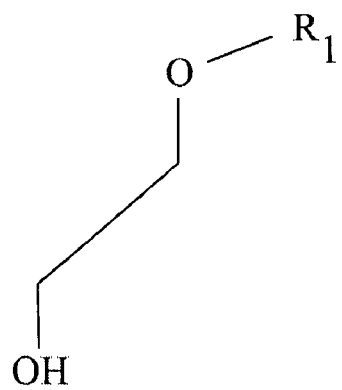

FIG. 6 provides chemical structures for particular ethylene glycol monoethers which can be utilized to produce embodiments of the inventive differential evaporation potentiated disinfection system.

Figure 7:
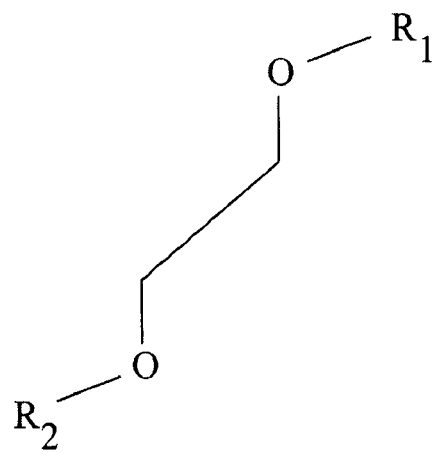

FIG. 7 provides chemical structures for particular ethylene glycol diethers which can be utilized to produce embodiments of the inventive differential evaporation potentiated disinfection system.

Figure 8:
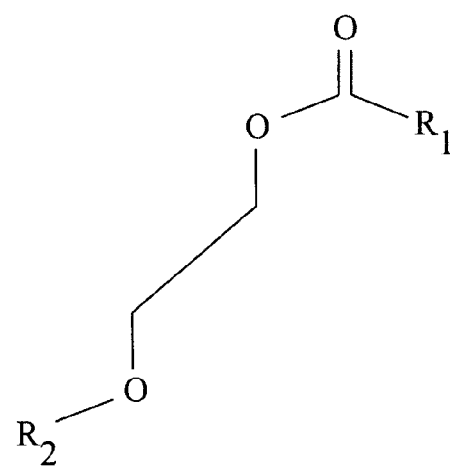

FIG. 8 provides chemical structures for particular ethylene glycol ether esters which can be utilized to produce embodiments of the inventive differential evaporation potentiated disinfection system.

Figure 9:
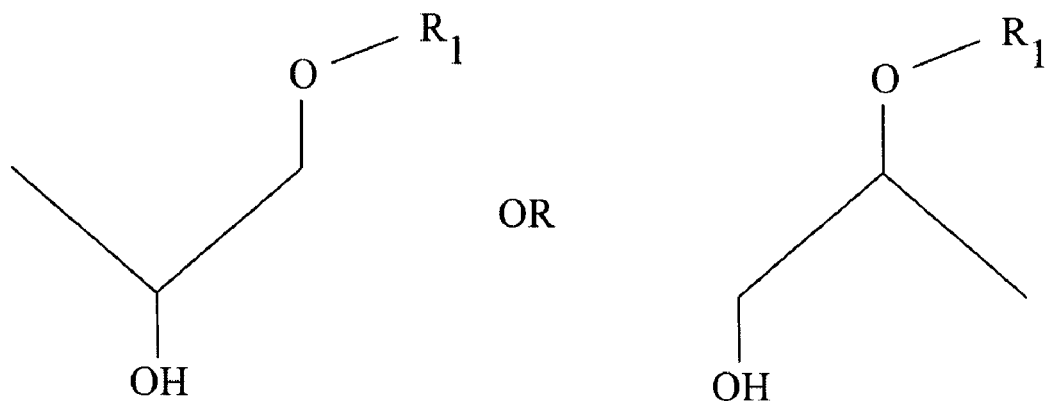

FIG. 9 provides chemical structures for particular propylene glycol monoethers which can be utilized to produce embodiments of the inventive differential evaporation potentiated disinfection system.

Figure 10:
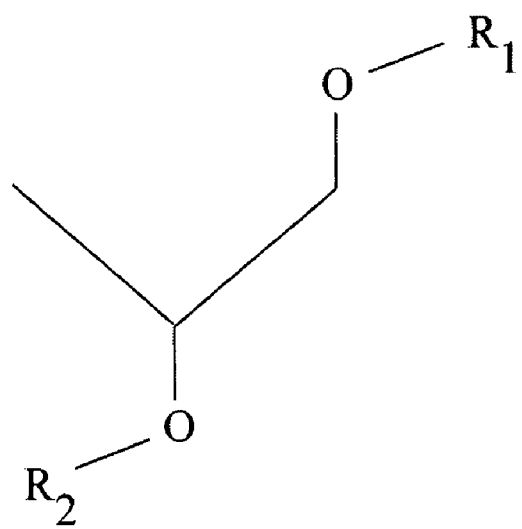

FIG. 10 provides chemical structures for particular propylene glycol diethers which can be utilized to produce embodiments of the inventive differential evaporation potentiated disinfection system.

Figure 11:
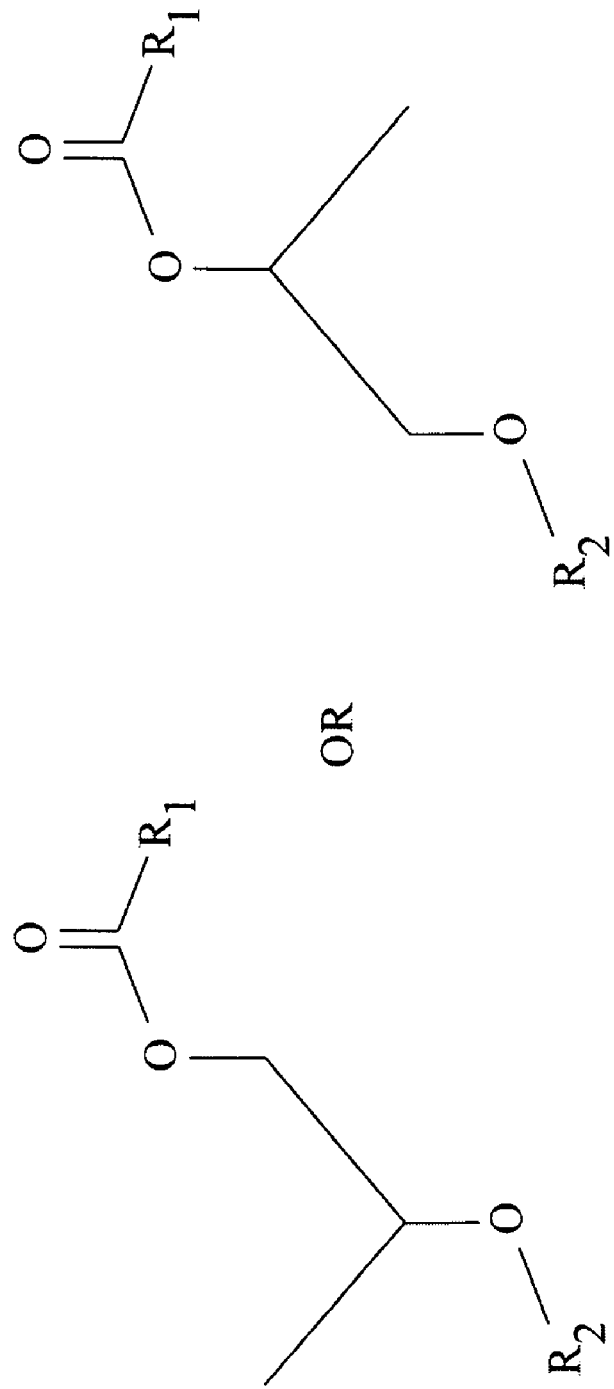

FIG. 11 provides chemical structures for particular propylene glycol ether esters which can be utilized to produce embodiments of the inventive differential evaporation potentiated disinfection system.

Figure 12:
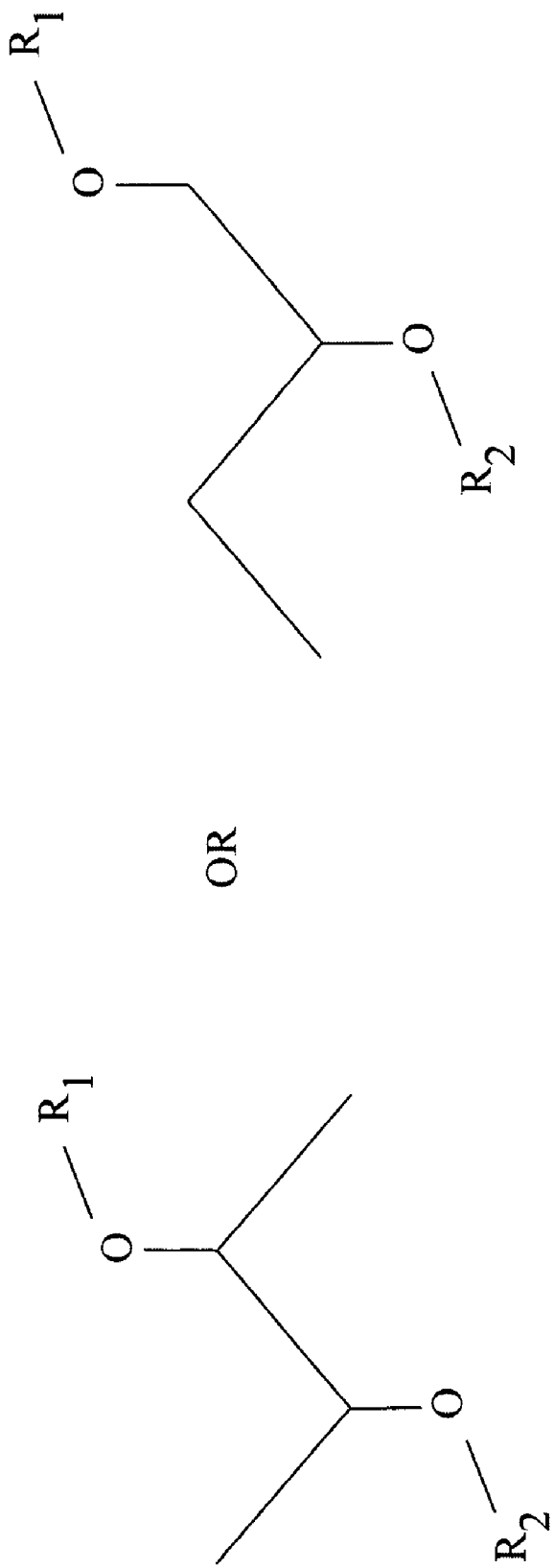

FIG. 12 provides chemical structures for particular butylene glycol monoethers which can be utilized to produce embodiments of the inventive differential evaporation potentiated disinfection system.

FIG. 13 provides chemical structures for particular butylene glycol diethers which can be utilized to produce embodiments of the inventive differential evaporation potentiated disinfection system.

Figure 14:
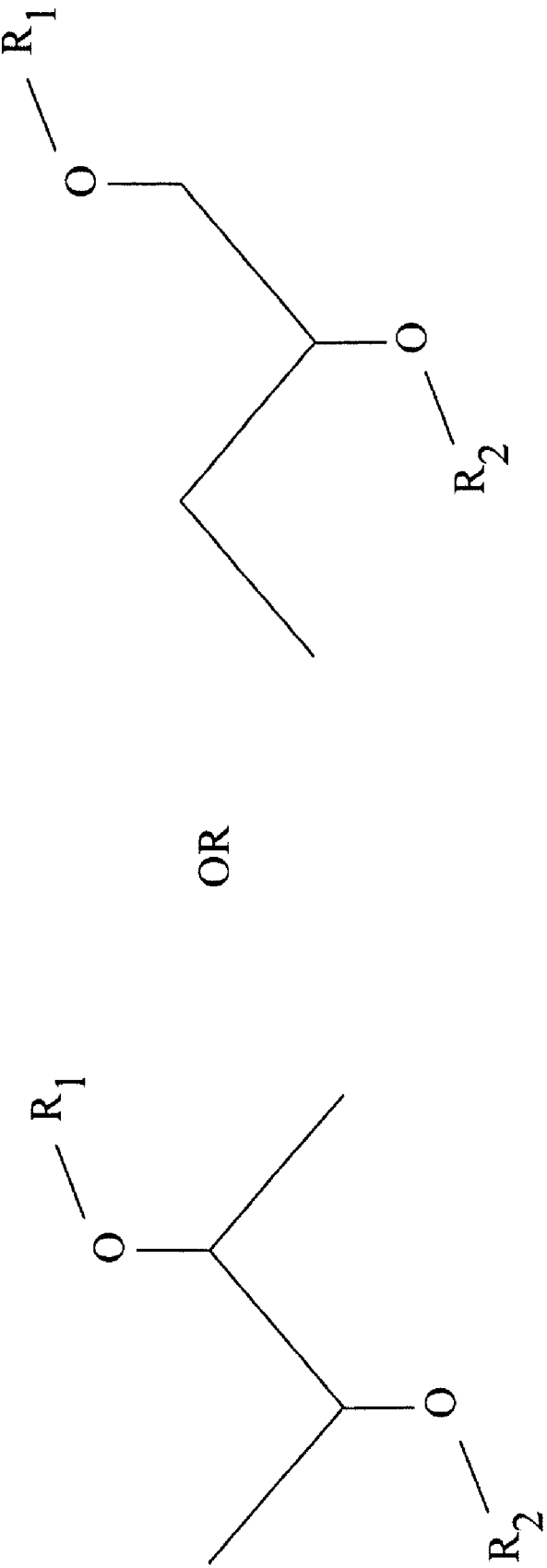

FIG. 14 provides chemical structures for particular butylene glycol monoether esters which can be utilized to produce embodiments of the inventive differential evaporation potentiated disinfection system.

Figure 15:
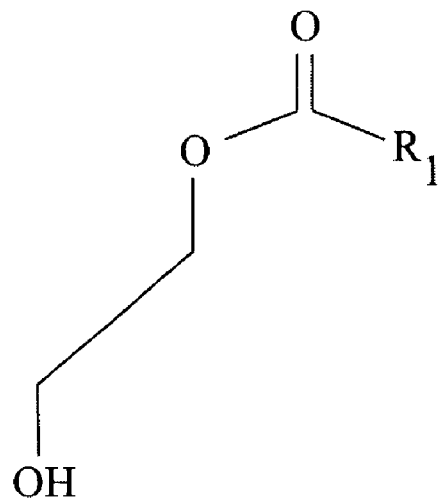

FIG. 15 provides chemical structures for particular ethylene glycol monoesters which can be utilized to produce embodiments of the inventive differential evaporation potentiated disinfection system.

Figure 16:
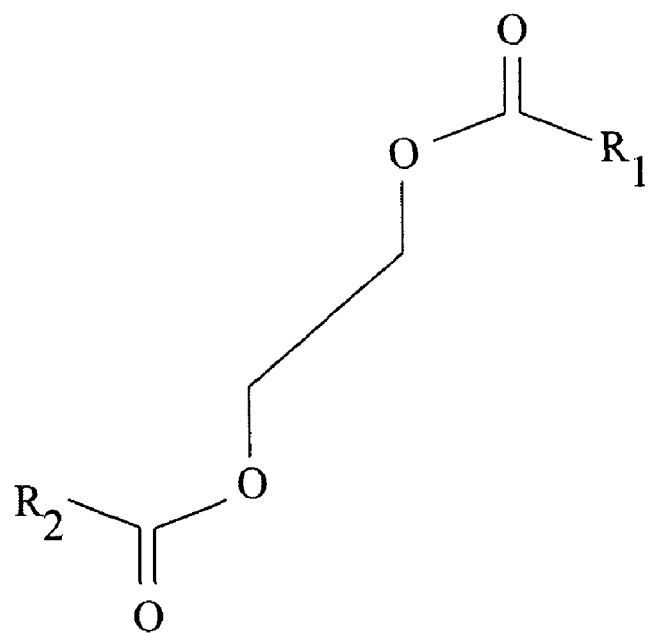

FIG. 16 provides chemical structures for particular ethylene glycol diesters which can be utilized to produce embodiments of the inventive differential evaporation potentiated disinfection system.

Figure 17:
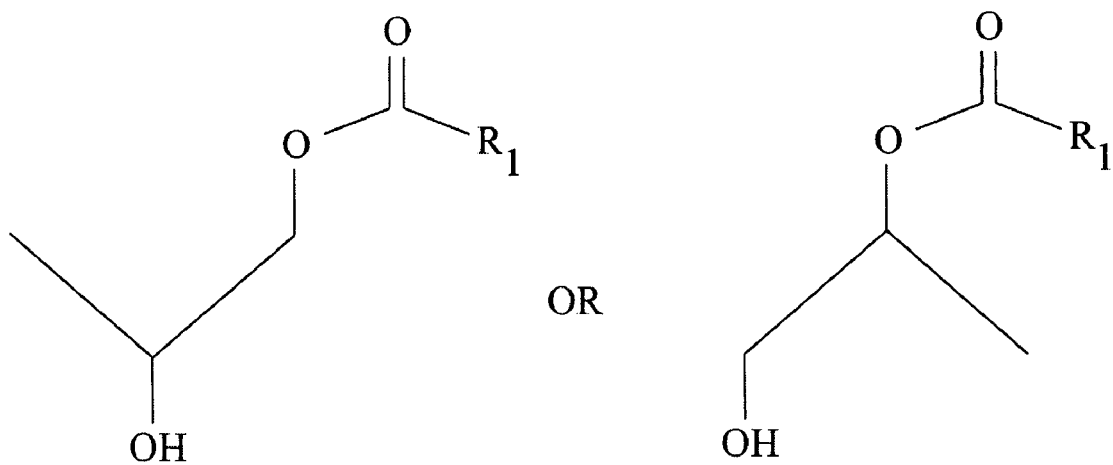

FIG. 17 provides chemical structures for particular propylene glycol monoesters which can be utilized to produce embodiments of the inventive differential evaporation potentiated disinfection system.

Figure 18:
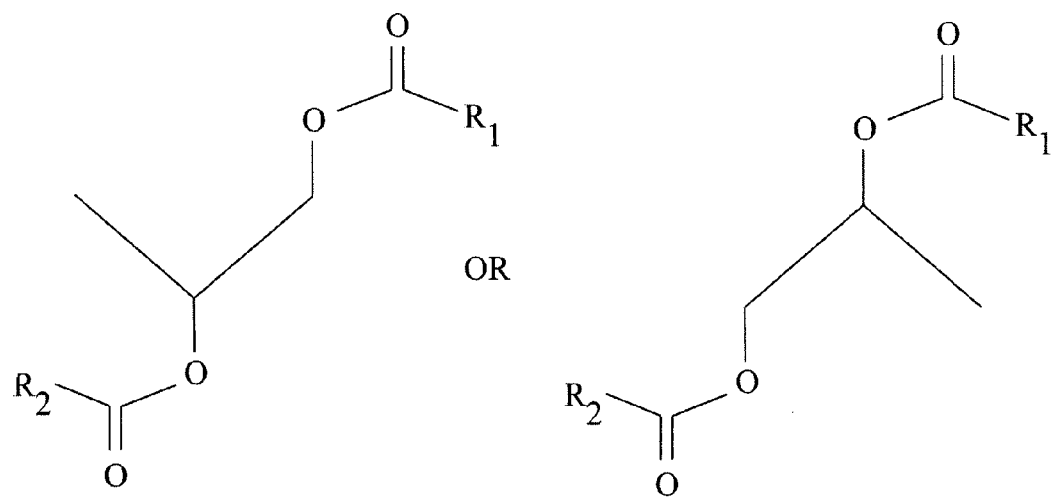

FIG. 18 provides chemical structures for particular propylene glycol diesters which can be utilized to produce embodiments of the inventive differential evaporation potentiated disinfection system.

Figure 19:
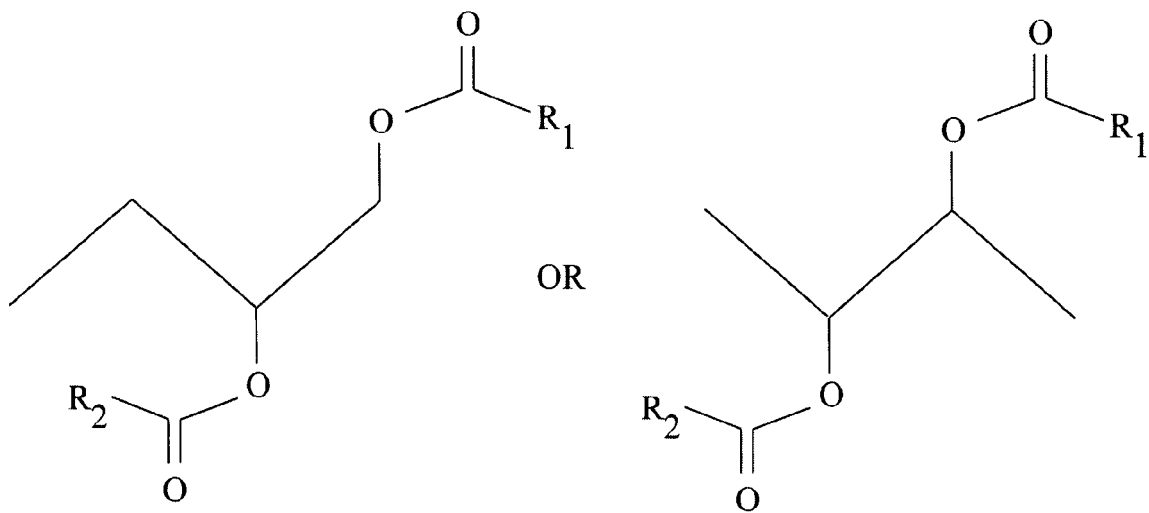

FIG. 19 provides chemical structures for particular propylene glycol diesters which can be utilized to produce embodiments of the inventive differential evaporation potentiated disinfection system.

Figure 20:
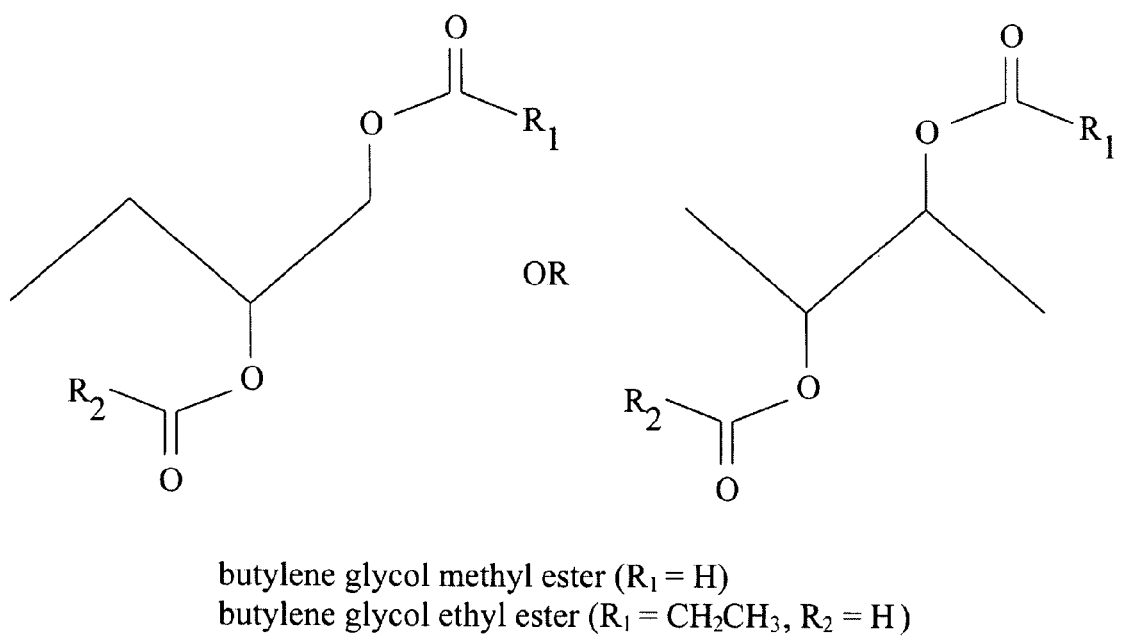

FIG. 20 provides chemical structures for particular butylene glycol esters which can be utilized to produce embodiments of the inventive differential evaporation potentiated disinfection system.

Figure 21:
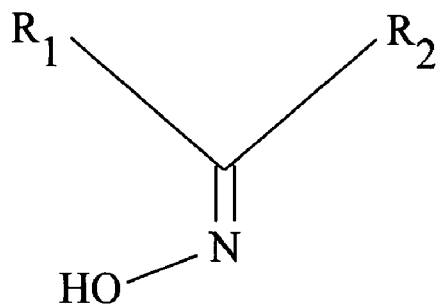

FIG. 21 provides chemical structures for particular oximes which can be utilized to produce embodiments of the inventive differential evaporation potentiated disinfection system.

FIG. 22 provides chemical structures for particular dimethylaminoalcohols which can be utilized to produce embodiments of the inventive differential evaporation potentiated disinfection system.

Figure 23:
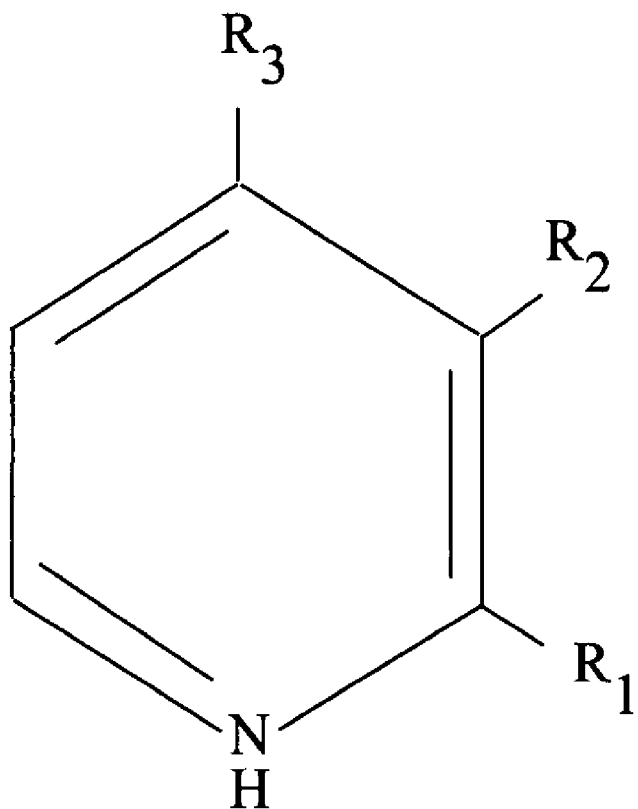

FIG. 23 provides chemical structures for particular pyridines which can be utilized to produce embodiments of the inventive differential evaporation potentiated disinfection system.

FIG. 24 provides chemical structures for particular aliphatic alcohols which can be utilized to produce embodiments of the inventive differential evaporation potentiated disinfection system.

V. DETAILED DESCRIPTION OF THE PREFERRED EMBODIMENTS

Generally, differential evaporation potentiated antimicrobial compositions and methods of using such differential evaporation potentiated antimicrobial compositions to provide a reduction in populations of viable microorganisms. Specifically, antimicrobial compositions which include an antimicrobially active agent soluble in an inactive agent with the antimicrobially active agent potentiated by differential evaporation providing reduction in a population of viable microorganisms.

Figure 3:
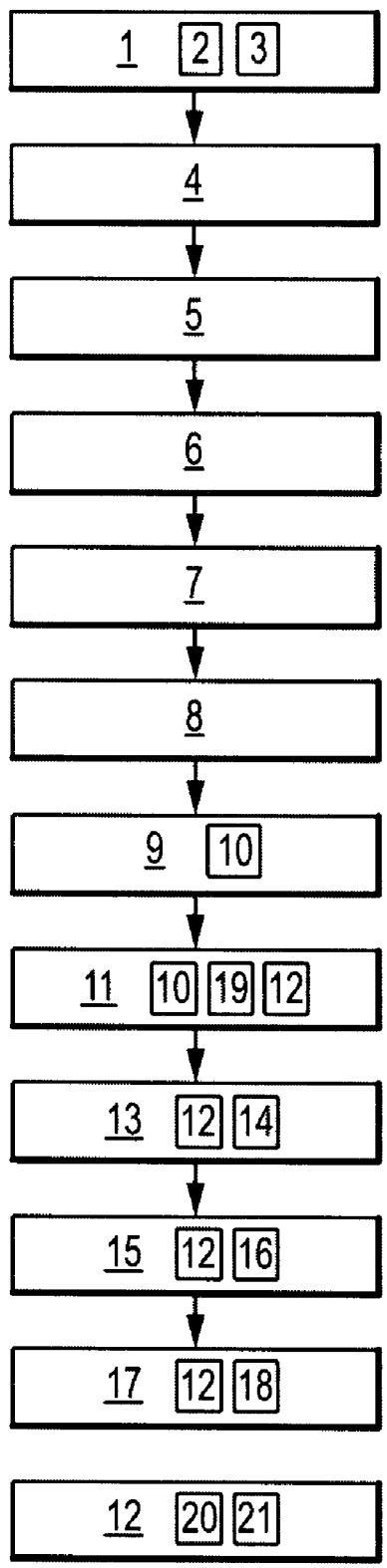
FIG. 3 is a block diagram which provides the steps of a particular method of selecting substances which can be utilized in embodiments of the inventive differential evaporation potentiated disinfection system.

Now referring primarily to FIG. 3, a block diagram provides the steps of a particular method of selecting substances which can be utilized in embodiments of the differential evaporation potentiated disinfection system. In a first selection step (1), a determination can be made as to whether an amount of substance (2) is fully miscible or highly soluble in an amount of water (3) at a temperature of between about 5° C. and about 90° C. at about 760 mm Hg. The miscibility of the amount of substance (2) and the amount of water (3) can be assessed by measuring the partition co-efficient of the amount of the substance solubilized in water under standard conditions of temperature and pressure.

If an amount of substance (2) can be shown to be fully miscible or highly soluble in an amount of water (3) as above described, then in a second selection step (4) a determination can be made as to whether the amount of substance (2) has a melting point at standard atmospheric pressure of below about 0° C. and more preferably below about −20° C. The melting point of the amount of substance can be determined by performing a melting point assessment as described in Product Properties Test Guidelines, OPPTS 830.7200, Melting Point/Melting Point Range, United States Environmental Protection Agency (1996), hereby incorporated by reference.

If the amount of substance (2) can be shown to have a melting point below about 0° C., then in a third selection step (5), a determination can be made as to whether the amount of substance has a boiling point at standard atmospheric pressure above about 110° C. and preferably above about 140° C. The boiling point of the amount of substance can be determined by performing a boiling point assessment as described in Product Properties Test Guidelines, OPPTS 830.7220, Boiling Point/Boiling Point Range, United States Environmental Protection Agency (1996), hereby incorporated by reference.

If the amount of substance (2) has a boiling point at standard atmospheric pressure above about 110° C., them in a fourth selection step (6) a determination can be made as to whether in the absence of water the amount of substance (2) has a flash point at standard atmospheric pressure that is above about 40° C. The flash point of the amount of substance can be determined by performing a flash point assessment as described in ASTM D7094-04 Standard Test Method for Flash Point by Modified Continuously Closed Cup (MCCCFP) Tester, ASTM International (2007), hereby incorporated by reference.

If in the absence of water, the amount of substance (2) has a flash point at standard atmospheric pressure that is above about 40° C., then in a fifth selection step (7) a determination can be made as to whether the amount of substance (2) when combined with the amount of water (3) has a flash point at standard atmospheric pressure above about 70° C. This flash-point assessment can be made as above-described.

If the amount of substance (2) when combined with the amount of water (3) has a flash point at standard atmospheric pressure above about 70° C., then in a sixth selection (8), a determination can be made as to whether the amount of substance (2) has Log P value of between about −0.20 and about +0.8. The Log P of the amount of substance (2) can be assessed by performing the Log P assessment as described by "Slow-stirred Method for Determining the n-Octanol/Water Partition Coefficient ($P_{ow}$) for Highly Hydrophobic Chemicals: Performance Evaluation in a Ring Test, Environmental Toxicology and Chemistry, Vol. 22, Issue 5 (May 2003).

Figure 1:
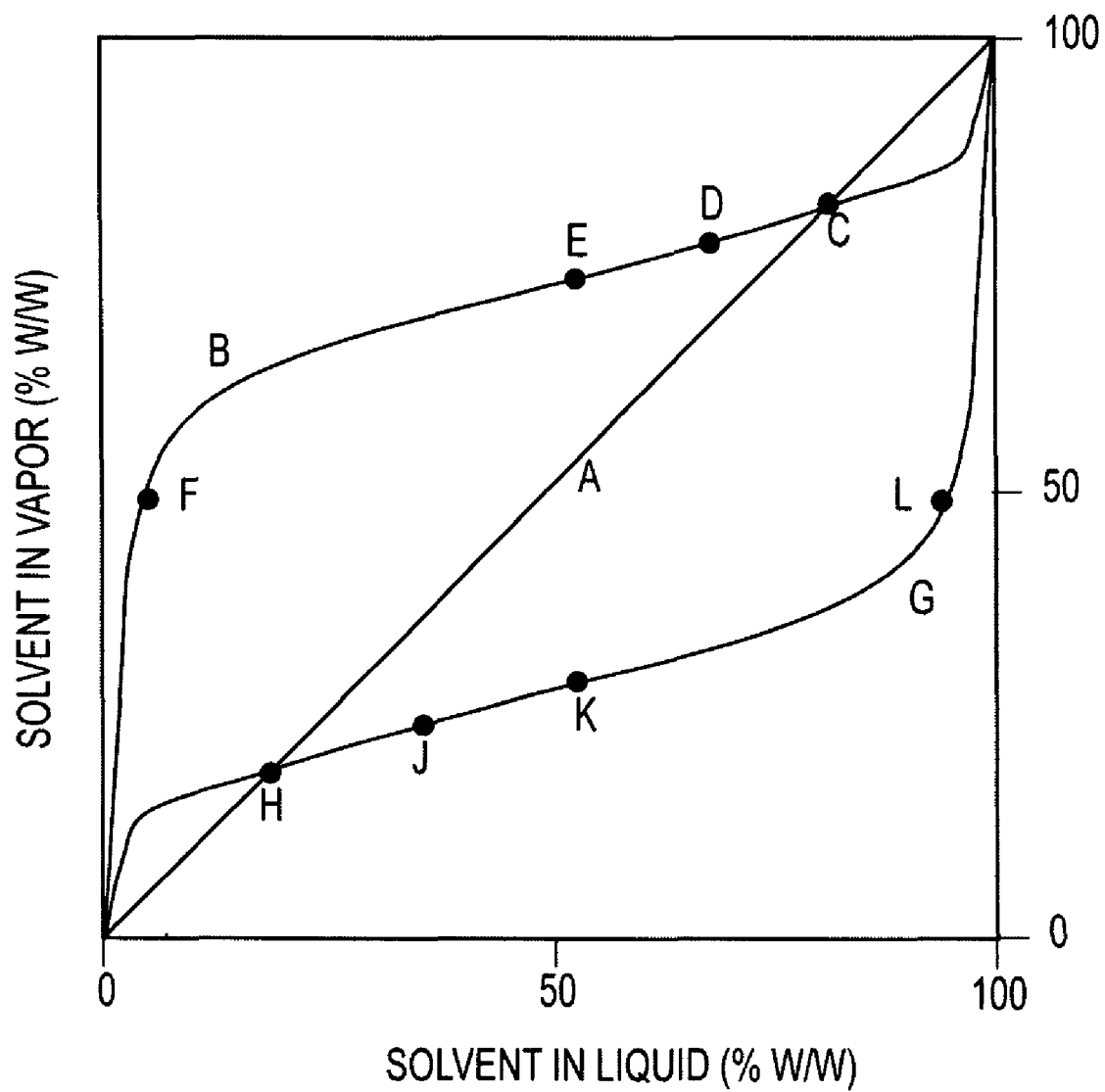
FIG. 1 is a vapor-liquid phase equilibria diagram which shows the relationship of the concentrations in liquid phase and vapor phase for one constituent.
Figure 2:
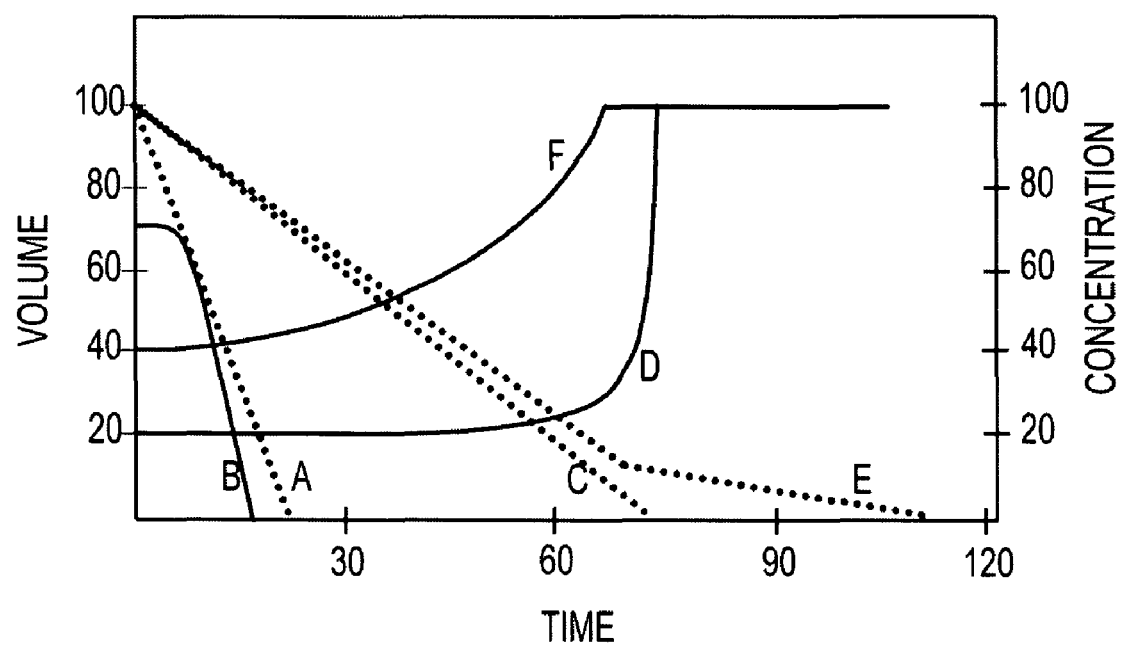
FIG. 2 is a diagram which shows the relationship between change in liquid phase concentration of a constituent and change in volume of the liquid phase for particular conventional and inventive mixtures.

If the amount of substance (2) has a Log P value of between about −0.20 and about +0.8, then in an seventh selection step (9), a determination can be made as to a range of concentrations of the amount of substance (2) combined with the amount of water (3) in which a differential evaporation potentiated composition (10) can be generated. The range can be assessed by generation of vapor-liquid phase equilibria as shown by FIG. 1 and as above-described.

If a range of concentrations of the amount of substance (2) generates a differential evaporation potentiated composition (10), then in an eighth selection step (11) a determination can be made as to whether the differential evaporation potentiated composition (10) identified provides a greater than a 2-$\log_{10}$ order reduction in a population of viable microorganisms (19) upon fluidic engagement to identify and isolate differential evaporation potentiated antimicrobial compositions (12). A particular non-limiting assay to determine whether the a differential evaporation potentiated compositions (10) further afford a differential evaporation potentiated antimicrobial compositions (12) is to provide cultures of microorganisms such as *Staphylococcus aureus* (ATCC 6538, MRI Sta 21), *Pseudomonas aeruginosa* (ATCC 9027, MRI PS 10, and *Salmonella Choleraesuis* (ATCC 13312, MRI SC 1 or other selected SC) prepared and suspended in Mueller Hinton Broth (MHB) to about 0.5 McFarland turbidity standard. These bacteria cultures can be diluted to obtain concentrations of about $10^7$ through about $10^3$ CFU/ml and 10 µl of each dilution can be spread onto a glass coverslip with a sterile loop and allowed to dry. Afterwards, the coverslips containing $10^5$ to $10^2$ CFU can be placed inside of petri dish. Different concentrations of the amount of substance can be applied to the cover slips with a nebulizer as described by Germicidal Spray Products as Disinfectants, Method 961.02, AOAC International (2004).

As a non-limiting example, isopropyl alcohol (IPA) and diacetone alcohol (DAA) can be assessed as above described by obtaining aqueous mixtures of IPA at concentrations of 55% w/w, 20% w/w, and 5% w/w. DAA can be assessed by providing concentrations of 60% w/w, 10% w/w, and 6% w/w in water. An amount of each concentration of IPA and DAA can be applied to a corresponding cover slip and evaporated to dryness. A nutrient agar lightly pressed against the coverslips allows contact of microorganisms on the coverslips with the nutrient agar. The nutrient agar can be incubated for 48 hours at 37° C. in contact with the coverslips and then observed for microbial reproduction in the region where the coverslips contact the nutrient agar. Untreated coverslips can be used as a positive control. Particular examples of utilizing the method are set forth below.

An additional ninth selection step (13) can include a determination as to whether the differential evaporation potentiated antimicrobial composition (12) identified in step 8 (11) evaporates to dryness without leaving a residue (14) whether because the amount of the differential evaporation potentiated antimicrobial composition (12) left on a treated surface after complete evaporation is not detectable or the amount of the differential evaporation potentiated antimicrobial composition (12) left on a treated surface after complete evaporation meets an accepted guideline for an industry as having evaporated without leaving a residue.

Again as an additional tenth selection step (15) a determination can be made as to whether each of the isolated differential evaporation potentiated antimicrobial compositions (12) pose any environmental, workplace, or health hazard concerns (16) sufficiently great to eliminate the isolated differential evaporation potentiated antimicrobial compositions (12) from being utilized to provide a greater than a 2-$\log_{10}$ order reduction in a population of viable microorganisms (19).

Again in an additional eleventh selection step (17) a determination can be made as to whether the cost per unit poses an economic barrier (18) to utilizing the isolated differential evaporation potentiated antimicrobial compositions (12) from being utilized to provide a greater than a 2-$\log_{10}$ order reduction in a population of viable microorganisms (19).

Again referring primarily to FIG. 3, by applying the method of selecting differential evaporation potentiated compositions to a numerous and varied plurality of substances (2), several groups of differential evaporation potentiated compositions (10) were identified which can be utilized as an antimicrobially active agent (20) soluble in an inactive agent (21) to produce numerous and varied differential evaporation potentiated antimicrobial compositions (12). However, the differential evaporation potentiated compositions (10) identified are not intended to be limiting with respect to use of the method to identify additional differential evaporation potentiated compositions (10) or limiting with respect to the scope of differential evaporation potentiated compositions (10) and differential evaporation potentiated antimicrobial compositions (12) encompassed by the invention. Rather, the particular method described is intended to provide the person of ordinary skill with a practical example of how to identify, make and use the numerous and wide variety of differential evaporation potentiated compositions (10) and differential evaporation potentiated antimicrobial compositions (12) described herein and which may be identified and isolated by alternate methods.

Now referring primarily to FIG. 4, differential evaporation potentiated compositions (10) can include an alpha hydroxyketone selected from the group consisting of: 3-hydroxy-2-butanone, 3-hydroxy-2-pentanone, 2-hydroxy-3-pentanone, 3-hydroxy-3-methyl-2-pentanone, 3-hydroxy-4-methyl-2-pentanone, 4-hydroxy-2-methyl-3-pentanone, 3-hydroxy-2-hexanone, 4-hydroxy-3-hexanone, 4-hydroxy-4-methyl-3-hexanone, 4-hydroxy-5-methyl-3-hexanone, 4-hydroxy-3-heptanone, 4-hydroxy-5-octanone.

An alpha hydroxyketone can provide an antimicrobially active agent (20) soluble in an inactive agent (21) such as water within a temperature range of between about 5° C. and about 90° C. at about 760 mm Hg, and having a boiling point greater than said inactive agent (21) of between about 10° C. and about 90° C. which allows the inactive agent (21) to evaporate from a mixture of the inactive agent (21) and the alpha hydroxyketone at a greater rate than the alpha hydroxyketone within the temperature range of between about 5° C. and about 90° C. at about 760 mm Hg, to provide a differential evaporation potentiated antimicrobial composition (12) which can provide greater than a 2-$\log_{10}$ order reduction in a population of viable microorganisms (19).

Now referring primarily to FIG. 5, differential evaporation potentiated compositions (10) can include a beta hydroxyketone selected from the group consisting of: 4-hydroxy-2-butanone, 4-hydroxy-2-pentanone, 1-hydroxy-3-pentanone, 4-hydroxy-4-methyl-2-pentanone (DAA), 4-hydroxy-2-hexanone, 5-hydroxy-4-methyl-3-hexanone, 5-hydroxy-5-methyl-3-hexanone, 5-hydroxy-3-heptanone, 5-hydroxy-5-methyl-3-heptanone, 3-hydroxy-3-methyl-5-heptanone, 4-hydroxy-3,4-dimethyl-2-hexanone.

A beta hydroxyketone can provide an antimicrobially active agent (20) soluble in an inactive agent (21) such as water within a temperature range of between about 5° C. and about 90° C. at about 760 mm Hg, and having a boiling point greater than said inactive agent (21) of between about 110° C. and about 90° C. which allows the inactive agent (21) to evaporate from a mixture of the inactive agent (21) and the beta hydroxyketone at a greater rate than the beta hydroxyketone within the temperature range of between about 5° C. and about 90° C. at about 760 mm Hg, to provide a differential evaporation potentiated antimicrobial composition (12) which can provide greater than a 2-$\log_{10}$ order reduction in a population of viable microorganisms (19).

As but one non-limiting example of a particular embodiments of an inventive differential evaporation potentiated antimicrobial composition (12), an amount of 4-hydroxy-4-methyl-2-pentanone (also referred to as "diacetone alcohol" or "DAA") can be combined with water to provide between about 10% and about 95% 4-hydroxy-4-methyl-2-pentanone (v/v), or between about 20% and about 95% 4-hydroxy-4-methyl-2-pentanone (v/v), or between about 20% and about 40% 4-hydroxy-4-methyl-2-pentanone (v/v), or not less than 10% 4-hydroxy-4-methyl-2-pentanone (v/v), or a concentration of 4-hydroxy-4-methyl-2-pentanone (v/v) above the azeotrope point which allows water to evaporate from the mixture at a greater rate than 4-hydroxy-4-methyl-2-pentanone.

Now referring primarily to Table 4 and FIG. 5, embodiments of the inventive differential evaporation potentiated antimicrobial composition (12) including DAA at various concentrations in water were tested as above-described and compared to various concentrations of IPA in water tested as above-described. As can be understood from the results set forth in Table 4, IPA at concentrations of 6% and 25% in water did not reduce the population of viable microorganisms. IPA and DAA at concentrations at which the IPA and the DAA evaporated from the mixture at a greater rate than the water performed similarly to reduce populations of microorganisms to less than 50% of the number of colonies counted in the corresponding positive control plate. DAA at concentrations at which water evaporated at a greater rate than DAA from the mixture provided greater reduction of populations of microorganisms than 70% IPA (v/v) and provided greater reduction of populations of microorganisms than concentrations of DAA which evaporated from the mixture at a greater rate than the water.

TABLE 4

| Active Component | % v/v | Inactive Component | % v/v | Evaporated from coverslip |
|---|---|---|---|---|
| Isopropanol | 70% | Water | 30% | X |
| Isopropanol | 25% | Water | 75% | ---o--- |
| Isopropanol | 6% | Water | 94% | ---o--- |
| DAA | 60% | Water | 40% | XXX |
| DAA | 10% | Water | 90% | XX |
| DAA | 6% | Water | 94% | X |

"XXX" denotes a plate in which zero colonies were present, representing complete reduction of the number of microorganisms (>5 $Log_{10}$ reduction).
"XXx" denotes a plate where the numbers of colonies represented less than 1% of the number of colonies counted in the corresponding positive control plate, representing nearly complete reduction of the number of microorganisms (>4 $Log_{10}$ reduction).
"XX" denotes a plate where the numbers of colonies represented less than 10% of the number of colonies counted in the corresponding positive control plate, representing a significant reduction of the number of microorganisms (>3 $Log_{10}$ reduction).
"X" denotes a plate where the numbers of colonies represented less than 50% of the number of colonies counted in the corresponding positive control plate, representing reduction of the number of microorganisms (<2 $Log_{10}$ reduction).
"---o---" denotes a plate where the numbers of colonies represented more than 50% of the number of colonies counted in the corresponding positive control plate, representing no significant reduction in the population of viable microorganisms (0 to 1 $Log_{10}$ reduction).

Now referring primarily to Table 5 and FIG. 5, DAA at concentrations of between about 3% and 15% in water (v/v) were comparatively tested for antimicrobial efficacy in a non-evaporative procedure and an evaporative procedure to provide a non-limiting example of evaporative potentiation of DAA. The non-evaporative and evaporative procedures included 50 μL of an overnight *Staphylococcus aureus* (ATCC 6538, ~$10^9$ CFU/mL) culture added to each 2 mL sterile plastic vial with a conical bottom and dried without capping in a centrifuge for 30 minutes. One hundred microliters of the solution being tested was added to each vial (as triplicate vials) either let set for 60 minutes (non-evaporative) or evaporated in a centrifuge for 60 minutes (evaporative), with time to evaporate being determined by each DAA mixtures own evaporative characteristic. To the non-evaporated vials, 400 μL Mueller Hinton Broth (MHB) was added to the vial and 100 μL was plated onto Nutrient agar (NA). To the evaporated vials, 500 μL of MHB was added and 100 μL was plated onto NA. Plates were incubated overnight at ~37° C. and counted (the "Potentiation Assay").

As can be understood from the results set forth in Table 5, DAA at all concentrations tested can be potentiated by evaporation. In contrast, IPA becomes less effective as an antimicrobial composition as evaporation occurs and cannot be potentiated.

TABLE 5

| Active Component | % v/v | Inactive Component | % v/v | Non-evaporated Log 10 Reduction | Evaporated Log 10 Reduction |
|---|---|---|---|---|---|
| DAA | 15% | Water | 85% | XXx | XXX |
| DAA | 10% | Water | 90% | --0-- | XX |
| DAA | 6% | Water | 94% | --0-- | X |
| DAA | 3% | Water | 97% | --0-- | X |
| IPA | 70% | Water | 30% | XXX | XXX |
| IPA | 20% | Water | 80% | XXX | --0-- |
| IPA | 10% | Water | 90% | --0-- | --0-- |

"XXX" denotes a plate in which zero colonies were present, representing complete reduction of the number of microorganisms (>5 $Log_{10}$ reduction).
"XXx" denotes a plate where the numbers of colonies represented less than 1% of the number of colonies counted in the corresponding positive control plate, representing nearly complete reduction of the number of microorganisms (>4 $Log_{10}$ reduction).
"XX" denotes a plate where the numbers of colonies represented less than 10% of the number of colonies counted in the corresponding positive control plate, representing a significant reduction of the number of microorganisms (>3 $Log_{10}$ reduction).
"X" denotes a plate where the numbers of colonies represented less than 50% of the number of colonies counted in the corresponding positive control plate, representing reduction of the number of microorganisms (<2 $Log_{10}$ reduction).
"--0--" denotes a plate where the numbers of colonies represented more than 50% of the number of colonies counted in the corresponding positive control plate, representing no significant reduction in the population of viable microorganisms (0 to 1 $Log_{10}$ reduction).

Now referring primarily to FIG. 6, differential evaporation potentiated compositions (10) can include an ethylene glycol monoether selected from the group consisting of: ethylene glycol monoethyl ether, ethylene glycol monopropyl ether, ethylene glycol monobutyl ether (EGMBE), ethylene glycol monopentyl ether, and ethylene glycol monohexyl ether.

An ethylene glycol monoether can provide an antimicrobially active agent (20) soluble in an inactive agent (21) such as water within a temperature range of between about 5° C. and about 90° C. at about 760 mm Hg, and having a boiling point greater than the inactive agent (20) of between about 10° C. and about 90° C. which allows the inactive agent (20) to evaporate from a mixture of the inactive agent (20) and the ethylene glycol monoether at a greater rate than the ethylene glycol monoether within the temperature range of between about 5° C. and about 90° C. at about 760 mm Hg, to provide a differential evaporation potentiated antimicrobial composition (12) which can provide greater than a 2-$log_{10}$ order reduction in a population of viable microorganisms (19).

Now referring primarily to Table 6 and FIG. 6, as a non-limiting example EGMBE at concentrations of between about between about 15% and about 95% in water (v/v) and more preferably between about 15% and about 30% in water (v/v) were comparatively tested for antimicrobial efficacy in a non-evaporative procedure and an evaporative procedure to provide a non-limiting example of evaporative potentiation of EGMBE by the Potentiation Assay above-described.

As can be understood from the results set forth in Table 6, certain concentrations of EGMBE tested can be potentiated by evaporation.

TABLE 6

| Active Component | % v/v | Inactive Component | % v/v | Non-evaporated Log 10 Reduction | Evaporated Log 10 Reduction |
|---|---|---|---|---|---|
| EGMBE | 15% | Water | 85% | XXX | XXX |
| EGMBE | 10% | Water | 90% | XXX | XXX |
| EGMBE | 5% | Water | 95% | --0-- | XX |

Now referring primarily to FIG. 7, differential evaporation potentiated compositions (10) can include an ethylene glycol diether selected from the group consisting of: ethylene glycol dimethyl ether, ethylene glycol diethyl ether, and ethylene glycol dipropyl ether.

The ethylene glycol diether can provide an antimicrobially active agent (20) soluble in an inactive agent (21) such as water within a temperature range of between about 5° C. and about 90° C. at about 760 mm Hg, and having a boiling point greater than the inactive agent (21) of between about 10° C. and about 90° C. which allows the inactive agent (21) to evaporate from a mixture of the inactive agent (21) and the ethylene glycol diether at a greater rate than the ethylene glycol diether within the temperature range of between about 5° C. and about 90° C. at about 760 mm Hg, to provide a differential evaporation potentiated antimicrobial composition (12) which can provide greater than a 2-$\log_{10}$ order reduction in a population of viable microorganisms (19).

Now referring primarily to FIG. 8, differential evaporation potentiated compositions (10) can include an ethylene glycol ether ester selected from the group consisting of: ethylene glycol monomethyl ether acetate (EGMEA), ethylene glycol monoethyl ether acetate, ethylene glycol monomethyl ether butyrate, and ethylene glycol monoethyl ether butyrate.

Now referring primarily to Table 7 and FIG. 8, as a non-limiting example EGMEA at concentrations of between about between about 15% and about 95% in water (v/v) and more preferably between about 15% and about 30% in water (v/v) were comparatively tested for antimicrobial efficacy in a non-evaporative procedure and an evaporative procedure to provide a non-limiting example of evaporative potentiation of EGMEA by the Potentiation Assay above-described.

As can be understood from the results set forth in Table 6, certain concentrations of EGMEA tested can be potentiated by evaporation.

TABLE 7

| Active Component | % v/v | Inactive Component | % v/v | Non-evaporated Log 10 Reduction | Evaporated Log 10 Reduction |
|---|---|---|---|---|---|
| EGMEA | 15% | Water | 85% | --0-- | XX |
| EGMEA | 10% | Water | 90% | --0-- | --0-- |
| EGMEA | 5% | Water | 95% | --0-- | --0-- |

Now referring primarily to FIG. 9, differential evaporation potentiated compositions (10) can include a propylene glycol monoether selected from the group consisting of: propylene glycol monomethyl ether, propylene glycol monoethyl ether, propylene glycol monopropyl ether, propylene glycol monobutyl ether, and propylene glycol monopentyl ether.

Now referring primarily to FIG. 10, differential evaporation potentiated compositions (10) can include a propylene glycol diether selected from the group consisting of: propylene glycol dimethyl ether, and propylene glycol diethyl ether.

Now referring primarily to FIG. 11 differential evaporation potentiated compositions (10) can include a propylene glycol ether ester selected from the group consisting of: propylene glycol monomethyl ether acetate, propylene glycol monoethyl ether acetate, propylene glycol monomethyl ether butyrate.

Now referring primarily to FIG. 12 differential evaporation potentiated compositions (10) can include a butylene glycol monoether selected from the group consisting of: butylene glycol monomethyl ether, butylene glycol monoethyl ether, butylene glycol monopropyl ether, and butylene glycol monobutyl ether.

Now referring primarily to FIG. 13 differential evaporation potentiated compositions (10) can include a butylene glycol diether selected from the group consisting of: butylene glycol dimethyl ether, and butylene glycol diethyl ether.

Now referring primarily to FIG. 14 differential evaporation potentiated compositions (10) can include a butylene glycol monoether ester selected from the group consisting of: butylene glycol monomethyl ether formate ester, and butylene glycol monoethyl ether acetate.

Now referring primarily to FIG. 15 differential evaporation potentiated compositions (10) can include an ethylene glycol monoester selected from the group consisting of: ethylene glycol monoethyl ester, ethylene glycol monopropyl ester, ethylene glycol monobutyl ester, ethylene glycol monopentyl ester, and ethylene glycol monohexyl ester.

As to the differential evaporation potentiated compositions (10) shown in FIGS. 9-15 including a propylene glycol monoether, a propylene glycol diether, a propylene glycol ether ester, a butylene glycol monoether, a propylene glycol diether, a butylene glycol monoether ester, or an ethylene glycol monoester, each can provide an antimicrobially active agent (20) soluble in an inactive agent such as water within a temperature range of between about 5° C. and about 90° C. at about 760 mm Hg, and having a boiling point greater than the inactive agent of between about 10° C. and about 90° C. which allows the inactive agent (21) to evaporate from a mixture of the inactive agent (21) and the propylene glycol monoether, propylene glycol diether, propylene glycol ether ester, butylene glycol monoether, propylene glycol diether, butylene glycol monoether ester, or ethylene glycol monoester, at a greater rate than the corresponding one of the antimicrobially active agents (20) within the temperature range of between about 5° C. and about 90° C. at about 760 mm Hg, to provide a differential evaporation potentiated antimicrobial composition (12) which can provide greater than a 2-$\log_{10}$ order reduction in a population of viable microorganisms (19).

Now referring primarily to FIG. 16, differential evaporation potentiated compositions (10) can include an ethylene glycol diester selected from the group consisting of: ethylene glycol dimethyl ester, ethylene glycol diethyl ester (EGDA) and ethylene glycol dipropyl ester.

Now referring primarily to Table 8 and FIG. 16, as a non-limiting example EGDA at concentrations of between about between about 15% and about 95% in water (v/v) and more preferably between about 10% and about 30% in water (v/v) were comparatively tested for antimicrobial efficacy in a non-evaporative procedure and an evaporative procedure to provide a non-limiting example of evaporative potentiation of EGDA by the Potentiation Assay above-described.

As can be understood from the results set forth in Table 8, certain concentrations of EGDA tested can be potentiated by evaporation.

TABLE 8

| Active Component | % v/v | Inactive Component | % v/v | Non-evaporated Log 10 Reduction | Evaporated Log 10 Reduction |
|---|---|---|---|---|---|
| EGDA | 15% | Water | 85% | --0-- | XX |
| EGDA | 10% | Water | 90% | --0-- | XX |
| EGDA | 5% | Water | 95% | --0-- | --0-- |

Now referring primarily to FIG. 17, differential evaporation potentiated compositions (10) can include a propylene glycol monoester selected from the group consisting of: propylene glycol monomethyl ester, propylene glycol monoethyl ester, propylene glycol monopropyl ester, propylene glycol monobutyl ester, and propylene glycol monopentyl ester.

Now referring primarily to FIG. 18, differential evaporation potentiated compositions (10) can include a propylene glycol diester selected from the group consisting of: propylene glycol dimethyl ester, propylene glycol diethyl ester, propylene glycol dipropyl ester, propylene glycol dibutyl ester, and propylene glycol dipentyl ester.

Now referring primarily to FIG. 19, differential evaporation potentiated compositions (10) can include a butylene glycol diester selected from the group consisting of: butylene glycol dimethyl ester, butylene glycol diethyl ester, butylene glycol dipropyl ester, or butylene propylene glycol dibutyl ester.

Now referring primarily to FIG. 20, differential evaporation potentiated compositions (10) can include a butylene glycol ester selected from the group consisting of: butylene glycol methyl ester, or butylene glycol ethyl ester.

The glycol ester, the propylene glycol monoester, the propylene glycol diester, the butylene glycol diester, the butylene glycol ester selected from the group can provide an antimicrobially active agent (20) soluble in an inactive agent (21) such as water within a temperature range of between about 5° C. and about 90° C. at about 760 mm Hg, and having a boiling point greater than the inactive agent of between about 10° C. and about 90° C. which allows the inactive agent (21) to evaporate from a mixture of the inactive agent (21) and the glycol ester, the propylene glycol monoester, the propylene glycol diester, the butylene glycol diester, or the butylene glycol ester at a greater rate than the corresponding one of the antimicrobially active agents (20) within the temperature range of between about 5° C. and about 90° C. at about 760 mm Hg, to provide a differential evaporation potentiated antimicrobial composition (12) which can provide greater than a 2-$\log_{10}$ order reduction in a population of viable microorganisms (19).

Now referring primarily to FIG. 21, differential evaporation potentiated compositions (10) can include an oxime selected from the group consisting of: 2-butanone oxime (MEKO), acetone oxime, methylethylketone oxime (MEKO), 2-pentanone oxime, 3-pentanone oxime, cyclopentanone oxime, 2-hexanone oxime, 3-hexanone oxime and cyclohexanone oxime.

Now referring primarily to Table 9 and FIG. 21, as a non-limiting example MEKO at concentrations of between about between about 15% and about 95% in water (v/v) and more preferably between about 10% and about 30% in water (v/v) were comparatively tested for antimicrobial efficacy in a non-evaporative procedure and an evaporative procedure to provide a non-limiting example of evaporative potentiation of EGDA by the Potentiation Assay above-described.

As can be understood from the results set forth in Table 9, certain concentrations of MEKO tested can be potentiated by evaporation.

TABLE 9

| Active Component | % v/v | Inactive Component | % v/v | Non-evaporated Log 10 Reduction | Evaporated Log 10 Reduction |
|---|---|---|---|---|---|
| MEKO | 15% | Water | 85% | XXX | XXX |
| MEKO | 10% | Water | 90% | XXX | XXX |
| MEKO | 5% | Water | 95% | X | X |

Now referring primarily to FIG. 21, differential evaporation potentiated compositions (10) can include a dimethylaminoalcohol selected from the group consisting of: 2-dimethylaminoethanol (DMEA), 2-dimethylamino-1-propanol, 1-dimethylamino-2-propanol, 1-dimethylamino-2-butanol and 3-dimethylamino-2-butanol.

Now referring primarily to Table 10 and FIG. 22, as a non-limiting example DMEA at concentrations of between about between about 15% and about 95% in water (v/v) and more preferably between about 10% and about 30% in water (v/v) were comparatively tested for antimicrobial efficacy in a non-evaporative procedure and an evaporative procedure to provide a non-limiting example of evaporative potentiation of DMEA by the Potentiation Assay above-described.

As can be understood from the results set forth in Table 10, certain concentrations of MEKO tested can be potentiated by evaporation.

TABLE 10

| Active Component | % v/v | Inactive Component | % v/v | Non-evaporated Log 10 Reduction | Evaporated Log 10 Reduction |
|---|---|---|---|---|---|
| DMEA | 15% | Water | 85% | --0-- | XXx |
| DMEA | 10% | Water | 90% | --0-- | XXx |
| DMEA | 5% | Water | 95% | --0-- | XX |

Now referring primarily to FIG. 23, differential evaporation potentiated compositions (10) can include a pyridine selected from the group consisting of: pyridine, 2-methylpyradine, 3-methylpyradine, 4-methylpyradine.

The pyridine selected from the group can provide an antimicrobially active agent (20) soluble in an inactive agent (21) such as water within a temperature range of between about 5° C. and about 90° C. at about 760 mm Hg, and having a boiling point greater than the inactive agent (21) of between about 10° C. and about 90° C. which allows the inactive agent (21) to evaporate from a mixture of the inactive agent (21) and the pyridine at a greater rate than the pyridine within the temperature range of between about 5° C. and about 90° C. at about 760 mm Hg, to provide a differential evaporation potentiated antimicrobial composition (12) which can provide greater than a 2-$\log_{10}$ order reduction in a population of viable microorganisms (19).

Now referring primarily to FIG. 24, differential evaporation potentiated compositions (10) can include an aliphatic alcohol selected from the group consisting of: 1-butanol and 2-butanol.

The aliphatic alcohol selected from the group can provide an antimicrobially active agent (20) soluble in an inactive agent (21) such as water within a temperature range of between about 5° C. and about 90° C. at about 760 mm Hg, and having a boiling point greater than the inactive agent (21) of between about 110° C. and about 90° C. which allows the inactive agent (21) to evaporate from a mixture of the inactive agent (21) and the butanol at a greater rate than the butanol within the temperature range of between about 5° C. and about 90° C. at about 760 mm Hg, to provide a differential evaporation potentiated antimicrobial composition (12) which can provide greater than a 2-$\log_{10}$ order reduction in a population of viable microorganisms (19).

As can be easily understood from the foregoing, the basic concepts of the present invention may be embodied in a variety of ways. The invention involves numerous and varied embodiments of a differential evaporation potentiated disinfectant system and methods of making and using such differential evaporation potentiated disinfectant system.

As such, the particular embodiments or elements of the invention disclosed by the description or shown in the figures accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "disinfectant" should be understood to encompass disclosure of the act of "disinfecting"—whether explicitly discussed or not—and, conversely, were there effectively disclosure of the act of "disinfecting", such a disclosure should be understood to encompass disclosure of a "disinfectant" and even a "means for disinfecting." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

Thus, the applicant(s) should be understood to claim at least: i) each of the differential evaporation potentiated compositions and differential evaporation potentiated antimicrobial compositions herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth below are intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. A method of reducing a viable microbial population comprising the steps of:
   a) combining an amount of water with an antimicrobials active agent to produce a differential evaporation potentiated antimicrobial composition said antimicrobials active agent miscible in said amount of water within a temperature range of about 5° C. and about 90° C., said antimicrobials active agent consisting essentially of a glycol ester selected from the group consisting of: an ethylene glycol monoester, an ethylene glycol diester, a propylene glycol monoester, propylene glycol diester, a butylene glycol monoester, and a butylene glycol diester, or combination thereof;
   b) applying said antimicrobial composition in a manner capable of contacting said viable antimicrobial population; and
   c) evaporating said amount of water from said antimicrobial composition within the temperature range of between about 5° C. and about 90° C. at a rate greater than said antimicrobials active agent evaporates from said antimicrobial composition, thereby increasing the percentage of said antimicrobials active agent during evaporation of said antimicrobial composition.

2. The method of reducing a viable microbial population of claim 1, wherein said population of viable microorganisms is reduced by greater than a 2-log 10 order.

3. The method of reducing a viable microbial population of claim 1, wherein said population of vial microorganism is reduced by greater than the 2-log 10 order during the period of time in which said amount of water evaporates from the antimicrobial composition.

4. The method of reducing a viable microbial population of claim 3, wherein said population of viable microorganisms is reduced by greater than the 2-log 10 order reduction in a said population of viable microorganisms by evaporation of said amount of water over a period of time.

5. The method of reducing a viable microbial population of claim 4, further comprising the step of providing an amount of said antimicrobials active agent in said antimicrobial composition sufficient to generate an azeotrope of the of said antimicrobials active agent in said amount of water.

6. The method of reducing a viable microbial population of claim 5, wherein evaporation of the said antimicrobial composition leaves no residue.

7. The method of reducing a viable microbial population of claim 1, wherein said antimicrobials active agent has a boiling point of between about 110° C. and about 180° C. and a melting point of not greater than −20° C.

8. The method of reducing a viable microbial population of claim 1, wherein the glycol ester is selected from the group consisting of: ethylene glycol monoethyl ester, ethylene glycol monopropyl ester, ethylene glycol monopentyl ester, ethylene glycol monohexyl ester, ethylene glycol dimethyl ester, ethylene glycol diethyl ester, ethylene glycol dipropyl ester, propylene glycol monomethyl ester, propylene glycol monoethyl ester, propylene glycol monopropyl ester, propylene glycol monobutyl ester, propylene glycol monpentyl ester, propylene glycol dimethyl ester, propylene glycol diethyl ester, propylene glycol dipropyl ester, propylene glycol dibutyl ester, propylene glycol dipentyl ester, butylene glycol methyl ester, butylene glycol ethyl ester, butylene glycol dimethyl ester, butylene glycol diethyl ester, butylene glycol dipropyl ester, and butylene glycol dibutyl ester.

9. The method of reducing a viable microbial population of claim 8, further comprising an amount of diluent which contains said population of viable microorganisms, said amount of diluent miscible in said antimicrobial composition.

10. The method of reducing a viable microbial population of claim 1, wherein the viable microorganisms are selected from the group consisting of: *Escherichia coli* (ATCC 25922, MRI EC 13), *Pseudomonas aeruginosa* (ATCC 9027, MRI Ps 10), *Staphylococcus aureus* (ATCC 6538, MRI Sta 21), *Aspergillus niger* (ATCC 16404, MRI AN 2), and *Clostridium* sporogenes (ATCC 19404, MRI Cl 12).

* * * * *

UNITED STATES PATENT AND TRADEMARK OFFICE
CERTIFICATE OF CORRECTION

| | | |
|---|---|---|
| PATENT NO. | : 8,119,688 B2 | |
| APPLICATION NO. | : 11/901915 | |
| DATED | : February 21, 2012 | |
| INVENTOR(S) | : Edwin Dean Neas and Thomas Boyd Gilligan | |

It is certified that error appears in the above-identified patent and that said Letters Patent is hereby corrected as shown below:

In the Claims

In column 18:

- line 24: following "combining an amount of water with an" please replace "antimicrobials" with --antimicrobially--;

- line 26: following "antimicrobial composition" please insert --,--;

- line 28: following "about 5° C" please remove ".";

- line 28: following "about 90° C" please remove ".";

- line 29: please replace "antimicrobials" with --antimicrobially--;

- line 40: following "about 5° C" please remove ".";

- line 40: following "about 90° C" please remove ".";

- line 41: please replace "antimicrobials" with --antimicrobially--;

- line 47: following "greater than a" please replace "2-log 10" with --2-$\log_{10}$--;

- line 49: following "wherein said population of" please replace "vial" with --viable--;

- line 50: following "greater than the" please replace "2-log 10" with --2-$\log_{10}$--;

- line 55: following "greater than the" please replace "2-log 10" with --2-$\log_{10}$--.

Signed and Sealed this
First Day of October, 2013

Teresa Stanek Rea
*Deputy Director of the United States Patent and Trademark Office*